United States Patent
Chen et al.

(10) Patent No.: US 12,116,600 B2
(45) Date of Patent: *Oct. 15, 2024

(54) MODIFIED TERMINAL DEOXYNUCLEOTIDYL TRANSFERASE (TdT) ENZYMES

(71) Applicant: Nuclera Ltd, Cambridge (GB)

(72) Inventors: Michael Chun Hao Chen, Cambridge (GB); Sihong Chen, Cambridge (GB); Gordon Ross McInroy, Cambridge (GB)

(73) Assignee: Nuclera Ltd., Cambridge (GB)

( * ) Notice: Subject to any disclaimer, the term of this patent is extended or adjusted under 35 U.S.C. 154(b) by 151 days.

This patent is subject to a terminal disclaimer.

(21) Appl. No.: 17/407,509

(22) Filed: Aug. 20, 2021

(65) Prior Publication Data

US 2022/0127588 A1    Apr. 28, 2022

(30) Foreign Application Priority Data

Aug. 21, 2020  (GB) .................................. 2013086

(51) Int. Cl.
*C12N 9/12*    (2006.01)

(52) U.S. Cl.
CPC .... *C12N 9/1264* (2013.01); *C12Y 207/07031* (2013.01)

(58) Field of Classification Search
CPC .................................................. C12N 9/1264
See application file for complete search history.

(56) References Cited

U.S. PATENT DOCUMENTS

| | | |
|---|---|---|
| 2016/0108382 A1 | 4/2016 | Efcavitch et al. |
| 2018/0023108 A1 | 1/2018 | Chen et al. |
| 2019/0078065 A1 | 3/2019 | Baiga et al. |
| 2020/0002690 A1 | 1/2020 | Ybert et al. |
| 2022/0119781 A1* | 4/2022 | Chen .................. C12N 9/1264 |

FOREIGN PATENT DOCUMENTS

| | | | |
|---|---|---|---|
| WO | 2018/215803 A1 | 11/2018 | |
| WO | WO-2020161480 A1 * | 8/2020 | ........... C12N 9/1264 |

OTHER PUBLICATIONS

Koiwai. Isolation and characterization of bovine and mouse terminal deoxynucleotidyltransferase cDNAs expressible in mammalian cells. Nucleic Acids Res. Jul. 25, 1986;14(14):5777-92.*
Fransceus. J Ind Microbiol Biotechnol. May 2017;44(4-5):687-695.*
Sanavia. Computational and Structural Biotechnology Journal, vol. 18, 2020, pp. 1968-1979.*
Studer. Residue mutations and their impact on protein structure and function: detecting beneficial and pathogenic changes. Biochem. J. (2013) 449, 581-594.*
Dominguez. DNA polymerase mu (Pol mu), homologous to TdT, could act as a DNA mutator in eukaryotic cells. EMBo J. Apr. 3, 2000;19(7):1731-42.*
Romain et al., Conferring a template-dependent polymerase activity to terminal deoxynucleotidyltransferase by mutations in the Loop1 region. Nucleic Acids Res. Aug. 2009;37(14):4642-56.

* cited by examiner

*Primary Examiner* — Yong D Pak
(74) *Attorney, Agent, or Firm* — McCarter & English, LLP; Yu Lu

(57) ABSTRACT

The invention relates to engineered terminal deoxynucleotidyl transferase (TdT) enzymes or the homologous amino acid sequence of Polµ, Polβ, Polλ, and Polθ of any species or the homologous amino acid sequence of X family polymerases of any species and uses thereof.

16 Claims, 4 Drawing Sheets
Specification includes a Sequence Listing.

FIG. 1

SEQUENCE LISTING

```
<160> NUMBER OF SEQ ID NOS: 18

<210> SEQ ID NO 1
<211> LENGTH: 509
<212> TYPE: PRT
<213> ORGANISM: Bos taurus

<400> SEQUENCE: 1

Met Asp Pro Leu Cys Thr Ala Ser Ser Gly Pro Arg Lys Lys Arg Pro
1               5                   10                  15

Arg Gln Val Gly Ala Ser Met Ala Ser Pro Pro His Asp Ile Lys Phe
            20                  25                  30

Gln Asn Leu Val Leu Phe Ile Leu Glu Lys Lys Met Gly Thr Thr Arg
        35                  40                  45

Arg Asn Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Glu Val Leu Glu Trp Leu Gln Val Gln Asn Ile Arg Ala Ser
                85                  90                  95

Ser Gln Leu Glu Leu Leu Asp Val Ser Trp Leu Ile Glu Ser Met Gly
            100                 105                 110

Ala Gly Lys Pro Val Glu Ile Thr Gly Lys His Gln Leu Val Val Arg
        115                 120                 125

Thr Asp Tyr Ser Ala Thr Pro Asn Pro Gly Phe Gln Lys Thr Pro Pro
    130                 135                 140

Leu Ala Val Lys Lys Ile Ser Gln Tyr Ala Cys Gln Arg Lys Thr Thr
145                 150                 155                 160

Leu Asn Asn Tyr Asn His Ile Phe Thr Asp Ala Phe Glu Ile Leu Ala
                165                 170                 175
```

-continued

```
Glu Asn Ser Glu Phe Lys Glu Asn Glu Val Ser Tyr Val Thr Phe Met
                180                 185                 190
Arg Ala Ala Ser Val Leu Lys Ser Leu Pro Phe Thr Ile Ile Ser Met
            195                 200                 205
Lys Asp Thr Glu Gly Ile Pro Cys Leu Gly Asp Lys Val Lys Cys Ile
210                 215                 220
Ile Glu Glu Ile Ile Glu Asp Gly Ser Ser Glu Val Lys Ala Val
225                 230                 235                 240
Leu Asn Asp Glu Arg Tyr Gln Ser Phe Lys Leu Phe Thr Ser Val Phe
                245                 250                 255
Gly Val Gly Leu Lys Thr Ser Glu Lys Trp Phe Arg Met Gly Phe Arg
            260                 265                 270
Ser Leu Ser Lys Ile Met Ser Asp Lys Thr Leu Lys Phe Thr Lys Met
            275                 280                 285
Gln Lys Ala Gly Phe Leu Tyr Tyr Glu Asp Leu Val Ser Cys Val Thr
        290                 295                 300
Arg Ala Glu Ala Glu Ala Val Gly Val Leu Val Lys Glu Ala Val Trp
305                 310                 315                 320
Ala Phe Leu Pro Asp Ala Phe Val Thr Met Thr Gly Gly Phe Arg Arg
                325                 330                 335
Gly Lys Lys Ile Gly His Asp Val Asp Phe Leu Ile Thr Ser Pro Gly
            340                 345                 350
Ser Ala Glu Asp Glu Glu Gln Leu Leu Pro Lys Val Ile Asn Leu Trp
        355                 360                 365
Glu Lys Lys Gly Leu Leu Leu Tyr Tyr Asp Leu Val Glu Ser Thr Phe
370                 375                 380
Glu Lys Phe Lys Leu Pro Ser Arg Gln Val Asp Thr Leu Asp His Phe
385                 390                 395                 400
Gln Lys Cys Phe Leu Ile Leu Lys Leu His His Gln Arg Val Asp Ser
                405                 410                 415
Ser Lys Ser Asn Gln Gln Glu Gly Lys Thr Trp Lys Ala Ile Arg Val
            420                 425                 430
Asp Leu Val Met Cys Pro Tyr Glu Asn Arg Ala Phe Ala Leu Leu Gly
        435                 440                 445
Trp Thr Gly Ser Arg Gln Phe Glu Arg Asp Ile Arg Arg Tyr Ala Thr
450                 455                 460
His Glu Arg Lys Met Met Leu Asp Asn His Ala Leu Tyr Asp Lys Thr
465                 470                 475                 480
Lys Arg Val Phe Leu Lys Ala Glu Ser Glu Glu Ile Phe Ala His
                485                 490                 495
Leu Gly Leu Asp Tyr Ile Glu Pro Trp Glu Arg Asn Ala
            500                 505
```

<210> SEQ ID NO 2
<211> LENGTH: 509
<212> TYPE: PRT
<213> ORGANISM: Artificial Sequence
<220> FEATURE:
<223> OTHER INFORMATION: Modified Bos Taurus Sequence

<400> SEQUENCE: 2

```
Met Asp Pro Leu Cys Thr Ala Ser Ser Gly Pro Arg Lys Lys Arg Pro
1               5                   10                  15
Arg Gln Val Gly Ala Ser Met Ala Ser Pro Pro His Asp Ile Lys Phe
            20                  25                  30
```

```
Gln Asn Leu Val Leu Phe Ile Leu Glu Lys Lys Met Gly Thr Thr Arg
         35                  40                  45

Arg Asn Phe Leu Met Glu Leu Ala Arg Arg Lys Gly Phe Arg Val Glu
         50                  55                  60

Asn Glu Leu Ser Asp Ser Val Thr His Ile Val Ala Glu Asn Asn Ser
 65                  70                  75                  80

Gly Ser Glu Val Leu Glu Trp Leu Gln Val Gln Asn Ile Arg Ala Ser
                 85                  90                  95

Ser Gln Leu Glu Leu Leu Asp Val Ser Trp Leu Ile Glu Ser Met Gly
             100                 105                 110

Ala Gly Lys Pro Val Glu Ile Thr Gly Lys His Gln Leu Val Val Arg
             115                 120                 125

Thr Asp Tyr Ser Ala Thr Pro Asn Pro Gly Phe Gln Lys Thr Pro Pro
         130                 135                 140

Leu Ala Val Lys Lys Ile Ser Gln Tyr Ala Cys Gln Arg Lys Thr Thr
145                 150                 155                 160

Leu Asn Asn Tyr Asn His Ile Phe Thr Asp Ala Phe Glu Ile Leu Ala
                 165                 170                 175

Glu Asn Ser Glu Phe Lys Glu Asn Glu Val Ser Tyr Val Thr Phe Met
             180                 185                 190

Arg Ala Ala Ser Val Leu Lys Ser Leu Pro Phe Thr Ile Ile Ser Met
         195                 200                 205

Lys Asp Thr Glu Gly Ile Pro Cys Leu Gly Asp Lys Val Lys Cys Ile
         210                 215                 220

Ile Glu Glu Ile Ile Glu Asp Gly Glu Ser Ser Glu Val Lys Ala Val
225                 230                 235                 240

Leu Asn Asp Glu Arg Tyr Gln Ser Phe Lys Leu Phe Thr Ser Val Phe
                 245                 250                 255

Gly Val Gly Leu Lys Thr Ser Glu Lys Trp Phe Arg Met Gly Phe Arg
             260                 265                 270

Ser Leu Ser Lys Ile Met Ser Asp Lys Thr Leu Lys Phe Thr Lys Met
         275                 280                 285

Gln Lys Ala Gly Phe Leu Tyr Tyr Glu Asp Leu Val Ser Cys Val Thr
         290                 295                 300

Arg Ala Glu Ala Glu Ala Val Gly Val Leu Val Lys Glu Ala Val Trp
305                 310                 315                 320

Ala Phe Leu Pro Asp Ala Phe Val Thr Met Thr Gly Gly Phe Arg Arg
                 325                 330                 335

Gly Lys Lys Ile Gly His Asp Val Asp Phe Leu Ile Thr Ser Pro Gly
             340                 345                 350

Ser Ala Glu Asp Glu Glu Gln Leu Leu Pro Lys Val Ile Asn Leu Trp
         355                 360                 365

Glu Lys Lys Gly Leu Leu Leu Tyr Tyr Asp Leu Val Glu Ser Thr Phe
370                 375                 380

Glu Lys Phe Lys Leu Pro Ser Arg Gln Val Asp Thr Leu Asp His Phe
385                 390                 395                 400

Gln Lys Cys Phe Leu Ile Leu Lys Leu His His Gln Arg Val Asp Ser
                 405                 410                 415

Ser Lys Ser Asn Gln Gln Glu Gly Lys Thr Trp Lys Ala Ile Arg Val
             420                 425                 430

Asp Leu Val Met Cys Pro Tyr Glu Asn Arg Ala Phe Ala Leu Leu Gly
         435                 440                 445
```

```
Trp Thr Gly Ser Arg Gln Phe Glu Arg Asp Ile Arg Arg Tyr Ala Thr
    450                 455                 460
His Glu Arg Lys Met Met Leu Asp Asn His Ala Leu Tyr Asp Lys Thr
465                 470                 475                 480
Lys Arg Val Phe Leu Lys Ala Glu Ser Glu Glu Ile Phe Ala His
            485                 490                 495
Leu Gly Leu Asp Tyr Ile Glu Pro Trp Glu Arg Asn Ala
            500                 505

<210> SEQ ID NO 3
<211> LENGTH: 361
<212> TYPE: PRT
<213> ORGANISM: Artificial Sequence
<220> FEATURE:
<223> OTHER INFORMATION: Truncated Protein Sequence 1

<400> SEQUENCE: 3

Lys Ile Ser Gln Tyr Ala Cys Gln Arg Lys Thr Thr Leu Asn Asn Tyr
1               5                   10                  15
Asn His Ile Phe Thr Asp Ala Phe Glu Ile Leu Ala Glu Asn Ser Glu
            20                  25                  30
Phe Lys Glu Asn Glu Val Ser Tyr Val Thr Phe Met Arg Ala Ala Ser
        35                  40                  45
Val Leu Lys Ser Leu Pro Phe Thr Ile Ile Ser Met Lys Asp Thr Glu
50                  55                  60
Gly Ile Pro Cys Leu Gly Asp Lys Val Lys Cys Ile Ile Glu Glu Ile
65                  70                  75                  80
Ile Glu Asp Gly Glu Ser Ser Glu Val Lys Ala Val Leu Asn Asp Glu
                85                  90                  95
Arg Tyr Gln Ser Phe Lys Leu Pro Thr Ser Val Phe Gly Val Gly Leu
            100                 105                 110
Lys Thr Ser Glu Lys Trp Phe Arg Met Gly Phe Arg Ser Leu Ser Lys
        115                 120                 125
Ile Met Ser Asp Lys Thr Leu Lys Phe Thr Lys Met Gln Lys Ala Gly
130                 135                 140
Phe Leu Tyr Tyr Glu Asp Leu Val Ser Cys Val Thr Arg Ala Glu Ala
145                 150                 155                 160
Glu Ala Val Gly Val Leu Val Lys Glu Ala Val Trp Ala Phe Leu Pro
                165                 170                 175
Asp Ala Phe Val Thr Met Thr Gly Gly Phe Arg Arg Gly Lys Lys Ile
            180                 185                 190
Gly His Asp Val Asp Phe Leu Ile Thr Ser Pro Gly Ser Ala Glu Asp
        195                 200                 205
Glu Glu Gln Leu Leu Pro Lys Val Ile Asn Leu Trp Glu Lys Lys Gly
210                 215                 220
Leu Leu Leu Tyr Tyr Asp Leu Val Glu Ser Thr Phe Glu Lys Phe Lys
225                 230                 235                 240
Leu Pro Ser Arg Gln Val Asp Thr Leu Asp His Phe Gln Lys Cys Phe
                245                 250                 255
Leu Ile Leu Lys Leu His His Gln Arg Val Asp Ser Ser Lys Ser Asn
            260                 265                 270
Gln Gln Glu Gly Lys Thr Trp Lys Ala Ile Arg Val Asp Leu Val Met
        275                 280                 285
Cys Pro Tyr Glu Asn Arg Ala Phe Ala Leu Leu Gly Trp Thr Gly Ser
290                 295                 300
```

Arg Gln Phe Glu Arg Asp Ile Arg Arg Tyr Ala Thr His Glu Arg Lys
305                 310                 315                 320

Met Met Leu Asp Asn His Ala Leu Tyr Asp Lys Thr Lys Arg Val Phe
            325                 330                 335

Leu Lys Ala Glu Ser Glu Glu Ile Phe Ala His Leu Gly Leu Asp
            340                 345                 350

Tyr Ile Glu Pro Trp Glu Arg Asn Ala
            355                 360

<210> SEQ ID NO 4
<211> LENGTH: 494
<212> TYPE: PRT
<213> ORGANISM: Lepisosteus oculatus

<400> SEQUENCE: 4

Met Leu His Ile Pro Ile Phe Pro Pro Ile Lys Lys Arg Gln Lys Leu
1               5                   10                  15

Pro Glu Ser Arg Asn Ser Cys Lys Tyr Glu Val Lys Phe Ser Glu Val
            20                  25                  30

Ala Ile Phe Leu Val Glu Arg Lys Met Gly Ser Ser Arg Arg Lys Phe
            35                  40                  45

Leu Thr Asn Leu Ala Arg Ser Lys Gly Phe Arg Ile Glu Asp Val Leu
    50                  55                  60

Ser Asp Ala Val Thr His Val Ala Glu Asp Asn Ser Ala Asp Glu
65                  70                  75                  80

Leu Trp Gln Trp Leu Gln Asn Ser Ser Leu Gly Asp Leu Ser Lys Ile
                85                  90                  95

Glu Val Leu Asp Ile Ser Trp Phe Thr Glu Cys Met Gly Ala Gly Lys
            100                 105                 110

Pro Val Gln Val Glu Ala Arg His Cys Leu Val Lys Ser Cys Pro Val
            115                 120                 125

Ile Asp Gln Tyr Leu Glu Pro Ser Thr Val Glu Thr Val Ser Gln Tyr
130                 135                 140

Ala Cys Gln Arg Arg Thr Thr Met Glu Asn His Asn Gln Ile Phe Thr
145                 150                 155                 160

Asp Ala Phe Ala Ile Leu Ala Glu Asn Ala Glu Phe Asn Glu Ser Glu
                165                 170                 175

Gly Pro Cys Leu Ala Phe Met Arg Ala Ala Ser Leu Leu Lys Ser Leu
            180                 185                 190

Pro His Ala Ile Ser Ser Ser Lys Asp Leu Glu Gly Leu Pro Cys Leu
            195                 200                 205

Gly Asp Gln Thr Lys Ala Val Ile Glu Asp Ile Leu Glu Tyr Gly Gln
210                 215                 220

Cys Ser Lys Val Gln Asp Val Leu Cys Asp Asp Arg Tyr Gln Thr Ile
225                 230                 235                 240

Lys Leu Phe Thr Ser Val Phe Gly Val Gly Leu Lys Thr Ala Glu Lys
                245                 250                 255

Trp Tyr Arg Lys Gly Phe His Ser Leu Glu Glu Val Gln Ala Asp Asn
            260                 265                 270

Ala Ile His Phe Thr Lys Met Gln Lys Ala Gly Phe Leu Tyr Tyr Asp
            275                 280                 285

Asp Ile Ser Ala Ala Val Cys Lys Ala Glu Ala Gln Ala Ile Gly Gln
290                 295                 300

Ile Val Glu Glu Thr Val Arg Leu Ile Ala Pro Asp Ala Ile Val Thr
305                 310                 315                 320

```
Leu Thr Gly Gly Phe Arg Arg Gly Lys Glu Cys Gly His Asp Val Asp
                325                 330                 335

Phe Leu Ile Thr Thr Pro Glu Met Gly Lys Glu Val Trp Leu Leu Asn
            340                 345                 350

Arg Leu Ile Asn Arg Leu Gln Asn Gln Gly Ile Leu Leu Tyr Tyr Asp
        355                 360                 365

Ile Val Glu Ser Thr Phe Asp Lys Thr Arg Leu Pro Cys Arg Lys Phe
370                 375                 380

Glu Ala Met Asp His Phe Gln Lys Cys Phe Ala Ile Ile Lys Leu Lys
385                 390                 395                 400

Lys Glu Leu Ala Ala Gly Arg Val Gln Lys Asp Trp Lys Ala Ile Arg
                405                 410                 415

Val Asp Phe Val Ala Pro Pro Val Asp Asn Phe Ala Phe Ala Leu Leu
            420                 425                 430

Gly Trp Thr Gly Ser Arg Gln Phe Glu Arg Asp Leu Arg Arg Phe Ala
        435                 440                 445

Arg His Glu Arg Lys Met Leu Leu Asp Asn His Ala Leu Tyr Asp Lys
    450                 455                 460

Thr Lys Lys Ile Phe Leu Pro Ala Lys Thr Glu Glu Asp Ile Phe Ala
465                 470                 475                 480

His Leu Gly Leu Asp Tyr Ile Asp Pro Trp Gln Arg Asn Ala
                485                 490

<210> SEQ ID NO 5
<211> LENGTH: 355
<212> TYPE: PRT
<213> ORGANISM: Artificial Sequence
<220> FEATURE:
<223> OTHER INFORMATION: Modified Spotted gar TdT Seq

<400> SEQUENCE: 5

Thr Val Ser Gln Tyr Ala Cys Gln Arg Thr Thr Met Glu Asn His
1               5                   10                  15

Asn Gln Ile Phe Thr Asp Ala Phe Ala Ile Leu Ala Glu Asn Ala Glu
            20                  25                  30

Phe Asn Glu Ser Glu Gly Pro Cys Leu Ala Phe Met Arg Ala Ala Ser
        35                  40                  45

Leu Leu Lys Ser Leu Pro His Ala Ile Ser Ser Lys Asp Leu Glu
    50                  55                  60

Gly Leu Pro Cys Leu Gly Asp Gln Thr Lys Ala Val Ile Glu Asp Ile
65                  70                  75                  80

Leu Glu Tyr Gly Gln Cys Ser Lys Val Gln Asp Val Leu Cys Asp Asp
                85                  90                  95

Arg Tyr Gln Thr Ile Lys Leu Phe Thr Ser Val Phe Gly Val Gly Leu
            100                 105                 110

Lys Thr Ala Glu Lys Trp Tyr Arg Lys Gly Phe His Ser Leu Glu Glu
        115                 120                 125

Val Gln Ala Asp Asn Ala Ile His Phe Thr Lys Met Gln Lys Ala Gly
    130                 135                 140

Phe Leu Tyr Tyr Asp Asp Ile Ser Ala Ala Val Cys Lys Ala Glu Ala
145                 150                 155                 160

Gln Ala Ile Gly Gln Ile Val Glu Glu Thr Val Arg Leu Ile Ala Pro
                165                 170                 175

Asp Ala Ile Val Thr Leu Thr Gly Gly Phe Arg Arg Gly Lys Glu Cys
            180                 185                 190
```

Gly His Asp Val Asp Phe Leu Ile Thr Thr Pro Glu Met Gly Lys Glu
    195                 200                 205

Val Trp Leu Leu Asn Arg Leu Ile Asn Arg Leu Gln Asn Gln Gly Ile
210                 215                 220

Leu Leu Tyr Tyr Asp Ile Val Glu Ser Thr Phe Asp Lys Thr Arg Leu
225                 230                 235                 240

Pro Cys Arg Lys Phe Glu Ala Met Asp His Phe Gln Lys Cys Phe Ala
                245                 250                 255

Ile Ile Lys Leu Lys Lys Glu Leu Ala Ala Gly Arg Val Gln Lys Asp
            260                 265                 270

Trp Lys Ala Ile Arg Val Asp Phe Val Ala Pro Val Asp Asn Phe
        275                 280                 285

Ala Phe Ala Leu Leu Gly Trp Thr Gly Ser Arg Gln Phe Glu Arg Asp
    290                 295                 300

Leu Arg Arg Phe Ala Arg His Glu Arg Lys Met Leu Leu Asp Asn His
305                 310                 315                 320

Ala Leu Tyr Asp Lys Thr Lys Lys Ile Phe Leu Pro Ala Lys Thr Glu
                325                 330                 335

Glu Asp Ile Phe Ala His Leu Gly Leu Asp Tyr Ile Asp Pro Trp Gln
            340                 345                 350

Arg Asn Ala
        355

<210> SEQ ID NO 6
<211> LENGTH: 530
<212> TYPE: PRT
<213> ORGANISM: Mus musculus

<400> SEQUENCE: 6

Met Asp Pro Leu Gln Ala Val His Leu Gly Pro Arg Lys Lys Arg Pro
1               5                   10                  15

Arg Gln Leu Gly Thr Pro Val Ala Ser Thr Pro Tyr Asp Ile Arg Phe
                20                  25                  30

Arg Asp Leu Val Leu Phe Ile Leu Glu Lys Lys Met Gly Thr Thr Arg
            35                  40                  45

Arg Ala Phe Leu Met Glu Leu Ala Arg Arg Lys Gly Phe Arg Val Glu
        50                  55                  60

Asn Glu Leu Ser Asp Ser Val Thr His Ile Val Ala Glu Asn Asn Ser
65                  70                  75                  80

Gly Ser Asp Val Leu Glu Trp Leu Gln Leu Gln Asn Ile Lys Ala Ser
                85                  90                  95

Ser Glu Leu Glu Leu Leu Asp Ile Ser Trp Leu Ile Glu Cys Met Gly
                100                 105                 110

Ala Gly Lys Pro Val Glu Met Met Gly Arg His Gln Leu Val Val Asn
            115                 120                 125

Arg Asn Ser Ser Pro Ser Pro Val Pro Gly Ser Gln Asn Val Pro Ala
        130                 135                 140

Pro Ala Val Lys Lys Ile Ser Gln Tyr Ala Cys Gln Arg Arg Thr Thr
145                 150                 155                 160

Leu Asn Asn Tyr Asn Gln Leu Phe Thr Asp Ala Leu Asp Ile Leu Ala
                165                 170                 175

Glu Asn Asp Glu Leu Arg Glu Asn Glu Gly Ser Cys Leu Ala Phe Met
            180                 185                 190

```
Arg Ala Ser Ser Val Leu Lys Ser Leu Pro Phe Pro Ile Thr Ser Met
        195                 200                 205
Lys Asp Thr Glu Gly Ile Pro Cys Leu Gly Asp Lys Val Lys Ser Ile
    210                 215                 220
Ile Glu Gly Ile Ile Glu Asp Gly Glu Ser Ser Glu Ala Lys Ala Val
225                 230                 235                 240
Leu Asn Asp Glu Arg Tyr Lys Ser Phe Lys Leu Phe Thr Ser Val Phe
            245                 250                 255
Gly Val Gly Leu Lys Thr Ala Glu Lys Trp Phe Arg Met Gly Phe Arg
            260                 265                 270
Thr Leu Ser Lys Ile Gln Ser Asp Lys Ser Leu Arg Phe Thr Gln Met
        275                 280                 285
Gln Lys Ala Gly Phe Leu Tyr Tyr Glu Asp Leu Val Ser Cys Val Asn
    290                 295                 300
Arg Pro Glu Ala Glu Ala Val Ser Met Leu Val Lys Glu Ala Val Val
305                 310                 315                 320
Thr Phe Leu Pro Asp Ala Leu Val Thr Met Thr Gly Gly Phe Arg Arg
            325                 330                 335
Gly Lys Met Thr Gly His Asp Val Asp Phe Leu Ile Thr Ser Pro Glu
        340                 345                 350
Ala Thr Glu Asp Glu Glu Gln Gln Leu Leu His Lys Val Thr Asp Phe
    355                 360                 365
Trp Lys Gln Gln Gly Leu Leu Leu Tyr Cys Asp Ile Leu Glu Ser Thr
370                 375                 380
Phe Glu Lys Phe Lys Gln Pro Ser Arg Lys Val Asp Ala Leu Asp His
385                 390                 395                 400
Phe Gln Lys Cys Phe Leu Ile Leu Lys Leu Asp His Gly Arg Val His
            405                 410                 415
Ser Glu Lys Ser Gly Gln Gln Glu Gly Lys Gly Trp Lys Ala Ile Arg
        420                 425                 430
Val Asp Leu Val Met Cys Pro Tyr Asp Arg Arg Ala Phe Ala Leu Leu
    435                 440                 445
Gly Trp Thr Gly Ser Arg Gln Phe Glu Arg Asp Leu Arg Arg Tyr Ala
            450                 455                 460
Thr His Glu Arg Lys Met Met Leu Asp Asn His Ala Leu Tyr Asp Arg
465                 470                 475                 480
Thr Lys Gly Lys Thr Val Thr Ile Ser Pro Leu Asp Gly Lys Val Ser
            485                 490                 495
Lys Leu Gln Lys Ala Leu Arg Val Phe Leu Glu Ala Glu Ser Glu Glu
        500                 505                 510
Glu Ile Phe Ala His Leu Gly Leu Asp Tyr Ile Glu Pro Trp Glu Arg
    515                 520                 525
Asn Ala
    530

<210> SEQ ID NO 7
<211> LENGTH: 20
<212> TYPE: PRT
<213> ORGANISM: Homo sapiens
```

<400> SEQUENCE: 7

Glu Ser Thr Phe Glu Lys Leu Arg Leu Pro Ser Arg Lys Val Asp Ala
1               5                   10                  15

Leu Asp His Phe
            20

<210> SEQ ID NO 8
<211> LENGTH: 19
<212> TYPE: PRT
<213> ORGANISM: Homo sapiens

<400> SEQUENCE: 8

His Ser Cys Cys Glu Ser Pro Thr Arg Leu Ala Gln Gln Ser His Met
1               5                   10                  15

Asp Ala Phe

<210> SEQ ID NO 9
<211> LENGTH: 494
<212> TYPE: PRT
<213> ORGANISM: Homo sapiens

<400> SEQUENCE: 9

Met Leu Pro Lys Arg Arg Arg Ala Arg Val Gly Ser Pro Ser Gly Asp
1               5                   10                  15

Ala Ala Ser Ser Thr Pro Pro Ser Thr Arg Phe Pro Gly Val Ala Ile
                20                  25                  30

Tyr Leu Val Glu Pro Arg Met Gly Arg Ser Arg Ala Phe Leu Thr
            35                  40                  45

Gly Leu Ala Arg Ser Lys Gly Phe Arg Val Leu Asp Ala Cys Ser Ser
    50                  55                  60

Glu Ala Thr His Val Val Met Glu Glu Thr Ser Ala Glu Glu Ala Val
65                  70                  75                  80

Ser Trp Gln Glu Arg Arg Met Ala Ala Pro Pro Gly Cys Thr Pro
                85                  90                  95

Pro Ala Leu Leu Asp Ile Ser Trp Leu Thr Glu Ser Leu Gly Ala Gly
                100                 105                 110

Gln Pro Val Pro Val Glu Cys Arg His Arg Leu Glu Val Ala Gly Pro
            115                 120                 125

Arg Lys Gly Pro Leu Ser Pro Ala Trp Met Pro Ala Tyr Ala Cys Gln
    130                 135                 140

Arg Pro Thr Pro Leu Thr His His Asn Thr Gly Leu Ser Glu Ala Leu
145                 150                 155                 160

Glu Ile Leu Ala Glu Ala Ala Gly Phe Glu Gly Ser Glu Gly Arg Leu
                165                 170                 175

Leu Thr Phe Cys Arg Ala Ala Ser Val Leu Lys Ala Leu Pro Ser Pro
            180                 185                 190

Val Thr Thr Leu Ser Gln Leu Gln Gly Leu Pro His Phe Gly Glu His
            195                 200                 205

Ser Ser Arg Val Val Gln Glu Leu Leu Glu His Gly Val Cys Glu Glu
    210                 215                 220

Val Glu Arg Val Arg Arg Ser Glu Arg Tyr Gln Thr Met Lys Leu Phe
225                 230                 235                 240

Thr Gln Ile Phe Gly Val Gly Val Lys Thr Ala Asp Arg Trp Tyr Arg
                245                 250                 255

```
Glu Gly Leu Arg Thr Leu Asp Asp Leu Arg Glu Gln Pro Gln Lys Leu
            260                 265                 270

Thr Gln Gln Gln Lys Ala Gly Leu Gln His His Gln Asp Leu Ser Thr
        275                 280                 285

Pro Val Leu Arg Ser Asp Val Asp Ala Leu Gln Val Val Glu Glu
290                 295                 300

Ala Val Gly Gln Ala Leu Pro Gly Ala Thr Val Thr Leu Thr Gly Gly
305                 310                 315                 320

Phe Arg Arg Gly Lys Leu Gln Gly His Asp Val Asp Phe Leu Ile Thr
                325                 330                 335

His Pro Lys Glu Gly Gln Glu Ala Gly Leu Leu Pro Arg Val Met Cys
            340                 345                 350

Arg Leu Gln Asp Gln Gly Leu Ile Leu Tyr His Gln His Gln His Ser
        355                 360                 365

Cys Cys Glu Ser Pro Thr Arg Leu Ala Gln Gln Ser His Met Asp Ala
    370                 375                 380

Phe Glu Arg Ser Phe Cys Ile Phe Arg Leu Pro Gln Pro Pro Gly Ala
385                 390                 395                 400

Ala Val Gly Gly Ser Thr Arg Pro Cys Pro Ser Trp Lys Ala Val Arg
                405                 410                 415

Val Asp Leu Val Val Ala Pro Val Ser Gln Phe Pro Phe Ala Leu Leu
            420                 425                 430

Gly Trp Thr Gly Ser Lys Leu Phe Gln Arg Glu Leu Arg Arg Phe Ser
        435                 440                 445

Arg Lys Glu Lys Gly Leu Trp Leu Asn Ser His Gly Leu Phe Asp Pro
    450                 455                 460

Glu Gln Lys Thr Phe Phe Gln Ala Ala Ser Glu Glu Asp Ile Phe Arg
465                 470                 475                 480

His Leu Gly Leu Glu Tyr Leu Pro Pro Glu Gln Arg Asn Ala
                485                 490

<210> SEQ ID NO 10
<211> LENGTH: 494
<212> TYPE: PRT
<213> ORGANISM: Pan paniscus

<400> SEQUENCE: 10

Met Leu Pro Lys Arg Arg Ala Arg Val Gly Ser Pro Ser Gly Asp
1               5                   10                  15

Ala Ala Ser Ser Thr Pro Pro Ser Thr Arg Phe Pro Gly Val Ala Ile
                20                  25                  30

Tyr Leu Val Glu Pro Arg Met Gly Arg Ser Arg Arg Ala Phe Leu Thr
            35                  40                  45

Arg Leu Ala Arg Ser Lys Gly Phe Arg Val Leu Asp Ala Cys Ser Ser
        50                  55                  60

Glu Ala Thr His Val Val Met Glu Glu Thr Ser Ala Glu Glu Ala Val
65                  70                  75                  80

Ser Trp Gln Glu Arg Arg Met Ala Ala Ala Pro Pro Gly Cys Thr Pro
                85                  90                  95

Pro Ala Leu Leu Asp Ile Ser Trp Leu Thr Glu Ser Leu Gly Ala Gly
            100                 105                 110

Gln Pro Val Pro Val Glu Cys Arg His Arg Leu Glu Val Ala Gly Pro
        115                 120                 125
```

Arg Lys Gly Pro Leu Ser Pro Ala Trp Met Pro Ala Tyr Val Cys Gln
130                 135                 140

Arg Pro Thr Pro Leu Thr His His Asn Thr Gly Leu Ser Glu Ala Leu
145                 150                 155                 160

Glu Thr Leu Ala Glu Ala Ala Gly Phe Glu Gly Ser Glu Gly Arg Leu
            165                 170                 175

Leu Thr Phe Cys Arg Ala Ala Ser Val Leu Lys Ala Leu Pro Ser Pro
            180                 185                 190

Val Thr Thr Leu Ser Gln Leu Gln Gly Leu Pro His Phe Gly Glu His
        195                 200                 205

Ser Ser Arg Val Val Gln Glu Leu Leu Glu His Gly Val Cys Glu Glu
210                 215                 220

Val Glu Arg Val Gln Arg Ser Glu Arg Tyr Gln Thr Met Lys Leu Phe
225                 230                 235                 240

Thr Gln Ile Phe Gly Val Gly Val Lys Thr Ala Asp Arg Trp Tyr Arg
                245                 250                 255

Glu Gly Leu Arg Thr Leu Asp Asp Leu Arg Glu Gln Pro Gln Lys Leu
            260                 265                 270

Thr Gln Gln Gln Lys Ala Gly Leu Gln His His Gln Asp Leu Ser Thr
        275                 280                 285

Pro Val Leu Arg Ser Asp Val Asp Ala Leu Gln Gln Val Val Glu Glu
290                 295                 300

Ala Val Gly Gln Ala Leu Pro Gly Ala Thr Val Thr Leu Thr Gly Gly
305                 310                 315                 320

Phe Arg Arg Gly Lys Leu Gln Gly His Asp Val Asp Phe Leu Ile Thr
                325                 330                 335

His Pro Lys Glu Gly Gln Glu Ala Gly Leu Leu Pro Arg Val Met Cys
            340                 345                 350

Arg Leu Gln Asp Gln Gly Leu Ile Leu Tyr His Gln His Gln His Ser
        355                 360                 365

Cys Trp Glu Ser Pro Thr Arg Leu Ala Gln Gln Ser His Met Asp Ala
370                 375                 380

Phe Glu Arg Ser Phe Cys Ile Phe Arg Leu Pro Gln Pro Pro Gly Ala
385                 390                 395                 400

Ala Val Gly Gly Ser Thr Arg Pro Cys Pro Ser Trp Lys Ala Val Arg
                405                 410                 415

Val Asp Leu Val Val Ala Pro Val Ser Gln Phe Pro Phe Ala Leu Leu
            420                 425                 430

Gly Trp Thr Gly Ser Lys Leu Phe Gln Arg Glu Leu Arg Arg Phe Ser
        435                 440                 445

Arg Lys Glu Lys Gly Leu Trp Leu Asn Ser His Gly Leu Phe Asp Pro
450                 455                 460

Glu Gln Lys Thr Phe Phe Gln Ala Ala Ser Glu Glu Asp Ile Phe Arg
465                 470                 475                 480

His Leu Gly Leu Glu Tyr Leu Pro Pro Glu Gln Arg Asn Ala
                485                 490

<210> SEQ ID NO 11
<211> LENGTH: 463
<212> TYPE: PRT
<213> ORGANISM: Artificial Sequence
<220> FEATURE:
<223> OTHER INFORMATION: Myotis brandtii AA Seq

<400> SEQUENCE: 11

```
Met Asn Ser Ala Pro Leu Ala Glu Pro Arg Leu Ala Gly Ala Glu Trp
1               5                   10                  15

Ser Arg Arg Val Ala Gly Leu Gly Thr Gly Ser Phe Pro Leu Pro Ser
            20                  25                  30

Ser Glu Val Thr His Val Val Met Glu Gln Thr Ser Ala Glu Glu Ala
        35                  40                  45

Val Arg Trp Gln Glu Ser Arg Pro Ala Pro Pro Gly Gly Thr His
    50                  55                  60

Pro Ala Leu Leu Asp Ile Ser Trp Phe Thr Glu Ser Met Ala Ala Gly
65                  70                  75                  80

Gln Pro Val Pro Val Glu Gly Arg His Cys Leu Gln Val Ala Val Ser
                85                  90                  95

Arg Glu Val Leu Pro Asn Pro Val Trp Met Pro Pro Tyr Ala Cys Gln
            100                 105                 110

Arg Pro Thr Pro Leu Thr His His Asn Thr Ser Leu Ser Glu Ala Leu
        115                 120                 125

Glu Met Leu Ala Glu Ala Ala Gly Phe Ala Gly Ser Glu Gly Arg Leu
130                 135                 140

Leu Ser Phe Ser Arg Ala Ala Ser Val Leu Lys Ala Leu Pro Cys Pro
145                 150                 155                 160

Val Thr Ala Leu Ser Gln Leu Gln Gly Leu Pro His Phe Gly His His
                165                 170                 175

Ser Cys Arg Val Ile Gln Glu Leu Leu Glu His Gly Val Cys Glu Glu
            180                 185                 190

Val Glu Arg Val Gln Arg Ser Glu Arg Tyr Gln Ser Met Lys Leu Phe
        195                 200                 205

Thr Arg Ile Phe Gly Val Gly Val Arg Thr Ala Asp Gln Trp Tyr Arg
210                 215                 220

Glu Gly Leu Arg Thr Leu Asp Asp Val Trp Lys Gln Val Gln Arg Leu
225                 230                 235                 240

Thr Gln Gln Gln Lys Ala Gly Leu Gln His Tyr Gln Asp Leu Ser Ser
                245                 250                 255

Pro Val Gln Arg Pro Asp Ala Glu Ala Leu Arg Gln Val Val Glu Ala
            260                 265                 270

Ala Val Gly Trp Ala Leu Pro Arg Ala Thr Val Thr Leu Ala Gly Gly
        275                 280                 285

Phe Arg Arg Gly Lys Leu Gln Gly His Asp Val Asp Phe Leu Ile Thr
290                 295                 300

His Pro Glu Glu Gly Gln Glu Val Gly Leu Leu Pro Arg Val Met His
305                 310                 315                 320

Tyr Leu Glu Gln Gln Gly Leu Val Leu Tyr Gln Gln His Gln Arg Ser
                325                 330                 335

Pro Ser Gly Asp Pro Ala Arg Leu Ala Pro Lys Gly His Ser Met Asp
            340                 345                 350

Thr Phe Glu Gln Ser Phe Cys Ile Phe Arg Leu Pro Arg Pro Pro Arg
        355                 360                 365

Thr Ala Glu Gly Gly Thr Trp Ser Pro His Pro Ser Trp Lys Ala Val
370                 375                 380

Arg Val Asp Leu Val Val Ala Pro Ile Ser Gln Phe Pro Phe Ala Leu
385                 390                 395                 400
```

```
Leu Gly Trp Thr Gly Ser Lys His Phe Glu Arg Glu Leu Arg Arg Phe
            405                 410                 415

Ser Arg Lys Glu Arg Gly Leu Trp Leu Asn Ser His Gly Leu Phe Asp
        420                 425                 430

Pro Glu Gln Lys Thr Phe Phe Gln Ala Ala Thr Glu Gly Asp Ile Phe
        435                 440                 445

Arg His Leu Gly Leu Ala Tyr Leu Pro Pro Glu Gln Arg Asn Ala
    450                 455                 460

<210> SEQ ID NO 12
<211> LENGTH: 517
<212> TYPE: PRT
<213> ORGANISM: Sarcophilus harrisii

<400> SEQUENCE: 12

Met His Arg Ile Arg Thr Thr Asp Ser Asp His Gly Lys Lys Arg Gln
1               5                   10                  15

Lys Lys Met Asp Ala Ile Ser Ser Lys Leu Tyr Glu Ile Lys Phe His
            20                  25                  30

Glu Phe Val Leu Phe Ile Leu Glu Lys Lys Met Gly Ala Thr Arg Arg
        35                  40                  45

Thr Phe Leu Met Asp Leu Ala Arg Lys Lys Gly Phe Arg Val Glu Ser
    50                  55                  60

Glu Leu Ser Asn Ser Val Thr His Ile Val Ala Glu Asn Asn Ser Gly
65                  70                  75                  80

Ser Asp Val Leu Ala Trp Leu Glu Ala His Lys Leu Glu Thr Thr Ala
            85                  90                  95

His Phe Glu Leu Leu Asp Val Ser Trp Leu Ile Glu Cys Met Lys Val
        100                 105                 110

Gly Lys Pro Val Asp Thr Lys Gly Lys Tyr Gln Leu Val Glu Ser Ser
    115                 120                 125

Ile Ala Ser Ala Asn Pro Asp Pro Asn Glu Gly Met Leu Lys Ile Gln
    130                 135                 140

Ser Pro Ala Met Asn Ala Ile Ser Pro Tyr Ala Cys Gln Arg Arg Thr
145                 150                 155                 160

Thr Leu Asn Asn His Asn Gln Arg Phe Thr Asp Ala Phe Glu Ile Leu
            165                 170                 175

Ala Lys Asn Tyr Glu Phe Arg Glu Asn His Gly His Cys Leu Thr Phe
        180                 185                 190

Leu Arg Ala Thr Ser Val Leu Lys Cys Leu Pro Phe Ala Ile Val Ser
    195                 200                 205

Met Lys Asp Ala Glu Gly Leu Pro Trp Ile Gly Asp Glu Val Lys Gly
    210                 215                 220

Ile Met Glu Glu Ile Ile Glu Asp Gly Gln Ser Leu Glu Val Gln Ala
225                 230                 235                 240

Val Leu Asn Asp Glu Arg Tyr Gln Ala Phe Lys Leu Phe Thr Ser Val
            245                 250                 255

Phe Gly Val Gly Leu Lys Thr Ala Glu Lys Trp Tyr Arg Met Gly Phe
        260                 265                 270

Arg Thr Leu Ser Lys Ile Gln Ser Asp Lys Ser Leu Lys Phe Thr Lys
    275                 280                 285

Met Gln Lys Ala Gly Phe Leu Tyr Tyr Glu Asp Leu Ile Ser Cys Val
    290                 295                 300
```

-continued

```
Ser Lys Ala Glu Ala Asp Ala Val Ser Leu Ile Val Lys Glu Ala Val
305                 310                 315                 320

Trp Thr Phe Leu Pro Asp Ala Leu Ile Thr Ile Thr Gly Gly Phe Arg
                325                 330                 335

Arg Gly Lys Glu Phe Gly His Asp Val Asp Phe Leu Ile Thr Ser Pro
            340                 345                 350

Gly Gly Glu Lys Glu Gln Val Asp Gln Leu Leu Gln Lys Val Thr Asn
        355                 360                 365

Leu Trp Glu Lys Gln Gly Leu Leu Tyr Tyr Asp Leu Met Glu Ser
370                 375                 380

Thr Phe Glu Asp Leu Lys Leu Pro Ser Arg Lys Val Asp Ala Leu Asp
385                 390                 395                 400

His Phe Gln Lys Cys Phe Leu Ile Leu Lys Leu Tyr Cys Gln Arg Gly
                405                 410                 415

Asp Arg Ser Lys Trp Glu Gly Pro Glu Gly Ser Asn Gly Leu Gln Thr
            420                 425                 430

Lys Asn Trp Lys Ala Ile Arg Val Asp Leu Val Val Cys Pro Tyr Asp
        435                 440                 445

Arg Tyr Ala Tyr Ala Leu Leu Gly Trp Ser Gly Ser Arg Gln Phe Glu
    450                 455                 460

Arg Asp Leu Arg Arg Tyr Ala Thr His Glu Lys Lys Met Met Leu Asp
465                 470                 475                 480

Asn His Ala Leu Tyr Asp Lys Thr Lys Arg Thr Phe Leu Lys Ala Glu
                485                 490                 495

Ser Glu Glu Glu Ile Phe Ser His Leu Gly Leu Glu Tyr Ile Glu Pro
            500                 505                 510

Trp Glu Arg Asn Ala
        515
```

<210> SEQ ID NO 13
<211> LENGTH: 497
<212> TYPE: PRT
<213> ORGANISM: Monodelphis domestica

<400> SEQUENCE: 13

```
Met Ala Ser Val Pro Leu Lys Arg Arg Gly Arg Ser Phe Gly Glu
1               5                   10                  15

Glu Ala Gln Gly Ala Ala Ala Pro Ser Pro Leu Ser Arg Phe Pro
                20                  25                  30

Glu Phe Thr Leu Tyr Leu Ala Glu Arg Arg Met Gly Arg Met Arg Arg
            35                  40                  45

Ala Phe Leu Thr Glu Leu Ala Arg Gly Lys Gly Phe Arg Val Asp Glu
        50                  55                  60

Val Tyr Ser Pro Gln Val Thr His Val Leu Met Glu Asp Ala Ser Gly
65                  70                  75                  80

Ala Glu Ala Ser Asp Tyr Leu Asp Arg Val Leu Gly Ala Ser Gln Ser
                85                  90                  95

Leu Gln Lys Pro Leu Leu Asp Ile Ser Trp Leu Thr Glu Ser Ile
            100                 105                 110

Gly Arg Gly Lys Pro Val Pro Val Glu Ala Lys Tyr Cys Leu Gly Ile
        115                 120                 125

Pro Glu Leu Leu Lys Asn Gln Val Pro Pro Val Ser Met Pro Ala Tyr
    130                 135                 140
```

```
Ala Cys Gln Arg His Thr Pro Leu Asn His Asn Phe His Leu Thr
145                 150                 155                 160

Glu Ala Leu Glu Thr Leu Ala Glu Ala Ala Asp Phe Glu Gly Ser Gln
            165                 170                 175

Gly Arg Phe Ile Ser Phe His Arg Ala Ala Ser Val Leu Lys Ala Leu
            180                 185                 190

Pro Asp Pro Ile Thr Asn Met Ser Gln Leu His Gly Leu Pro His Ile
            195                 200                 205

Gly Asp His Ser Ser Arg Ile Ile Gln Glu Leu Leu Glu His Gly Val
210                 215                 220

Ser Asn Glu Val Glu Thr Ile Lys Leu Ser Lys Arg Tyr Gln Thr Met
225                 230                 235                 240

Lys Leu Phe Thr Gln Ile Phe Gly Val Gly Val Lys Thr Ala Asp Arg
            245                 250                 255

Trp Tyr Gln Glu Gly Leu Arg Thr Leu Asp Asp Leu Gln Lys His Ser
            260                 265                 270

Arg Lys Leu Thr Arg Gln Gln Glu Ala Gly Ile His His Phe Glu Asp
            275                 280                 285

Leu Asn Thr Pro Val Tyr Arg His Glu Ala Asp Ala Ile Gln Gln Ile
290                 295                 300

Val Glu Glu Val Val Gln Gln Met Leu Pro Gly Ala Arg Val Ile Leu
305                 310                 315                 320

Ala Gly Gly Phe Arg Arg Gly Lys Pro His Gly His Asp Val Asp Phe
            325                 330                 335

Leu Ile Thr His Pro Val Glu Gly Leu Glu Ala Gly Leu Leu Ser Lys
            340                 345                 350

Val Met Gly Arg Leu Glu Ser Gln Gly Leu Val Leu Tyr Arg His Thr
            355                 360                 365

Gln Ser Pro Lys Asn Pro Asp Asn Thr Ala Phe Gln Ser Thr Ala Met
370                 375                 380

Asp Asp Tyr Glu Lys Cys Phe Ser Ile Leu Trp Phe Pro Lys Ser Pro
385                 390                 395                 400

Thr Thr Ser Ser His Leu Glu Ala Gly Glu Ser Ser Arg Asp Gly Lys
            405                 410                 415

Ala Val Arg Val Asp Phe Val Val Thr Pro Ile Ser Gln Phe Ala Phe
            420                 425                 430

Ala Leu Leu Gly Trp Thr Gly Ser Gln Tyr Phe Glu Arg Glu Leu Arg
            435                 440                 445

Arg Phe Ser Leu Asn Glu Lys Arg Leu Leu Leu Asn Asn His Gly Leu
            450                 455                 460

Tyr Asn Pro Glu Lys Lys Glu Thr Leu Pro Ala Ala Ser Glu Glu Asp
465                 470                 475                 480

Ile Phe Lys His Leu Gly Leu Asp Tyr Ile Pro Pro Glu Gln Arg Asn
            485                 490                 495

Ala
```

<210> SEQ ID NO 14
<211> LENGTH: 491
<212> TYPE: PRT
<213> ORGANISM: Otolemur garnetti

<400> SEQUENCE: 14

```
Met Leu Pro Lys Arg Arg Arg Ala Arg Ile Gly Ser Pro Gly Gly Asn
1               5                   10                  15
```

-continued

Ala Ala Ser Ser Glu Arg Pro Ser Thr Arg Phe Pro Gly Ile Thr Ile
            20                  25                  30

Tyr Leu Val Glu Arg Arg Met Gly Arg Ser Arg Arg Ala Phe Leu Thr
        35                  40                  45

Arg Leu Ala Arg Ser Lys Gly Phe Arg Val Leu Asp Ala Cys Ser Ser
50                  55                  60

Glu Val Thr His Ile Val Met Glu Gln Thr Ser Ala Glu Glu Ala Val
65                  70                  75                  80

Cys Trp Gln Glu His Arg Ala Thr Ala Ala Pro Ser Glu Cys Thr Pro
                85                  90                  95

Ala Thr Leu Leu Asp Ile Ser Trp Leu Thr Glu Ser Leu Ala Ala Gly
            100                 105                 110

Gln Pro Val Pro Met Glu Ser Arg His Arg Leu Glu Val Ala Glu Pro
        115                 120                 125

Arg Lys Ala Pro Pro Ser Ser Ile Trp Met Pro Ala Tyr Ala Cys Gln
130                 135                 140

Arg Pro Thr Pro Leu Thr His His Asn Ile Ser Leu Ser Glu Ala Leu
145                 150                 155                 160

Glu Thr Leu Ala Glu Ala Ala Gly Phe Glu Gly Arg Glu Gly His Ser
                165                 170                 175

Leu Thr Phe Leu Arg Ala Ala Ser Val Leu Arg Ala Leu Pro Arg Pro
            180                 185                 190

Val Val Ala Leu Thr Gln Leu Arg Gly Leu Pro His Phe Gly Glu His
        195                 200                 205

Ser Phe Arg Val Val Gln Glu Leu Leu Glu His Gly Val Cys Glu Glu
210                 215                 220

Val Glu Arg Val Arg His Ser Glu Arg Phe Gln Thr Met Lys Leu Phe
225                 230                 235                 240

Thr Gln Ile Phe Gly Val Gly Val Arg Thr Ala Asp Arg Trp Tyr Gln
                245                 250                 255

Glu Gly Leu Arg Thr Leu Asp Asp Leu Arg Glu Gln Pro Gln Arg Leu
            260                 265                 270

Thr Gln Gln Gln Lys Ala Gly Val Gln Tyr Tyr Gln Asp Leu Ser Thr
        275                 280                 285

Pro Val Leu Gln Pro Asp Ala Glu Ala Leu Gln Gln Leu Val Glu Ala
290                 295                 300

Ala Val Glu Gln Val Leu Ser Gly Ala Thr Val Thr Leu Thr Gly Gly
305                 310                 315                 320

Phe Arg Arg Gly Lys Leu Gln Gly His Asp Val Asp Phe Leu Ile Thr
                325                 330                 335

His Pro Glu Glu Gly Gln Glu Ala Gly Leu Leu Pro Arg Val Ile Arg
            340                 345                 350

Cys Leu Gln Asp Gln Gly Leu Val Leu Tyr Gln Gln Tyr Gln His Ser
        355                 360                 365

Leu Tyr Gly Ala Pro Gly His His Ser His Thr Met Asp Ala Phe Glu
370                 375                 380

Arg Ser Phe Cys Ile Phe Arg Leu Pro Gln Pro Gly Ala Ser Val
385                 390                 395                 400

Arg Glu Asp Pro Ser Cys Pro Ala Trp Lys Ala Val Arg Val Asp Leu
                405                 410                 415

Val Val Ala Pro Ile Ser Gln Phe Pro Phe Ala Leu Leu Gly Trp Thr
            420                 425                 430

```
Gly Ser Lys Leu Phe Gln Arg Glu Leu Arg Arg Phe Ser Arg Lys Glu
            435                 440                 445

Lys Gly Leu Cys Leu Asn Ser His Gly Leu Phe Asn Pro Glu Gln Asn
450                 455                 460

Thr Val Phe His Val Ala Ser Glu Glu Asp Ile Phe Arg His Leu Gly
465                 470                 475                 480

Leu Glu Tyr Leu Pro Pro Glu Gln Arg Asn Ala
                485                 490

<210> SEQ ID NO 15
<211> LENGTH: 510
<212> TYPE: PRT
<213> ORGANISM: Chinchilla laniger

<400> SEQUENCE: 15

Met Asp Pro Leu Gln Ala Ala His Ser Gly Pro Arg Lys Lys Arg Pro
1               5                   10                  15

Arg Gln Thr Gly Thr Leu Met Val Ser Pro His Asp Val Arg Phe
            20                  25                  30

Gly Asp Leu Val Leu Phe Ile Leu Glu Lys Lys Met Gly Thr Thr Arg
            35                  40                  45

Arg Ala Phe Leu Met Glu Leu Ala Arg Arg Lys Gly Phe Arg Val Glu
        50                  55                  60

Asn Glu Leu Ser Asp Ser Val Thr His Ile Val Ala Glu Asn Asn Ser
65                  70                  75                  80

Gly Asn Asp Val Leu Glu Trp Leu Gln Val Gln Asn Ile Gln Ala Ser
                85                  90                  95

Ser Arg Leu Glu Leu Leu Asp Val Ser Trp Leu Ile Glu Cys Met Gly
            100                 105                 110

Ala Gly Lys Pro Val Glu Met Thr Gly Lys His Gln Leu Leu Val Arg
            115                 120                 125

Arg Asp Tyr Pro Ala Ser Pro Lys Pro Gly Pro Gln Lys Thr Pro Ser
        130                 135                 140

Leu Ala Val Gln Lys Ile Ser Glu Tyr Ala Cys Gln Arg Arg Thr Thr
145                 150                 155                 160

Leu Asn Asn Cys Asn Cys Ile Phe Thr Asn Ala Phe Glu Ile Leu Ala
                165                 170                 175

Glu Asn Cys Glu Phe Arg Glu Asn Glu Ser Ser Tyr Val Thr Tyr Met
            180                 185                 190

Arg Ala Ala Ser Val Leu Lys Ser Leu Pro Phe Thr Ile Ile Ser Met
        195                 200                 205

Lys Asp Thr Glu Gly Ile Pro Cys Leu Gly Glu Lys Val Lys Cys Ile
    210                 215                 220

Ile Glu Glu Ile Ile Glu Asp Gly Glu Ser Glu Val Asn Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Lys Trp Phe Arg Met Gly Phe Arg
            260                 265                 270

Ser Leu Asn Lys Ile Lys Ser Asp Lys Ser Leu Lys Phe Thr Arg Met
        275                 280                 285

Gln Lys Ala Gly Phe Leu Tyr Tyr Glu Asp Leu Val Ser Cys Val Thr
    290                 295                 300

Arg Ala Glu Ala Glu Ala Val Ser Met Leu Val Lys Glu Ala Val Trp
305                 310                 315                 320
```

Ala Phe Leu Pro Gly Ala Phe Ile Ser Met Thr Gly Phe Arg Arg
                325                 330                 335

Gly Lys Glu Ile Gly His Asp Val Asp Phe Leu Ile Thr Ser Pro Glu
            340                 345                 350

Val Thr Glu Asp Glu Lys Gln Gln Leu Leu His Lys Val Ile Ser Leu
        355                 360                 365

Trp Glu Lys Lys Gly Leu Leu Leu Tyr Ser Asp Leu Val Glu Ser Thr
    370                 375                 380

Phe Glu Lys Leu Lys Leu Pro Ser Arg Lys Val Asp Ala Leu Asp His
385                 390                 395                 400

Phe Gln Lys Cys Phe Leu Ile Leu Lys Leu His Gln Arg Val Asp
                405                 410                 415

Ser Asp Lys Ser Pro Gln Gln Gly Gly Lys Thr Trp Lys Ala Ile Arg
            420                 425                 430

Val Asp Leu Val Val Cys Pro Tyr Glu Arg Arg Ala Phe Ala Leu Leu
        435                 440                 445

Gly Trp Thr Gly Ser Arg Gln Phe Glu Arg Asp Leu Arg Arg Tyr Ala
    450                 455                 460

Thr His Glu Arg Lys Met Met Leu Asp Asn His Ala Leu Tyr Asp Lys
465                 470                 475                 480

Thr Lys Arg Ile Phe Leu Lys Ala Glu Ser Glu Glu Glu Ile Phe Ala
                485                 490                 495

His Leu Gly Leu Asp Tyr Ile Glu Pro Trp Glu Arg Asn Ala
            500                 505                 510

<210> SEQ ID NO 16
<211> LENGTH: 510
<212> TYPE: PRT
<213> ORGANISM: Sus scrofa

<400> SEQUENCE: 16

Met Asp Pro Pro Gln Thr Val Pro Ser Ser Pro Arg Lys Lys Arg Pro
1               5                   10                  15

Arg Gln Val Gly Ala Ser Met Ala Ser Pro Ala His Asn Ile Lys Phe
            20                  25                  30

Arg Glu Leu Val Leu Phe Ile Leu Glu Lys Lys Met Gly Thr Thr Arg
        35                  40                  45

Arg Thr Phe Leu Met Glu Leu Ala Arg Arg Lys Gly Phe Arg Val Glu
    50                  55                  60

Asn Glu Leu Ser Asp Ser Val Thr His Ile Val Ala Glu Asn Asn Ser
65                  70                  75                  80

Gly Ser Glu Val Leu Glu Trp Leu Gln Ala Gln Lys Ile Arg Ala Ser
                85                  90                  95

Ser Gln Leu Thr Leu Leu Asp Val Ser Trp Leu Ile Glu Ser Met Gly
            100                 105                 110

Ala Gly Lys Pro Val Glu Met Thr Gly Lys His Gln Leu Val Val Arg
        115                 120                 125

Thr Asp Cys Ser Ala Ser Pro Ser Pro Gly Ser Gln Asn Thr Leu Pro
    130                 135                 140

Pro Ala Val Lys Lys Ile Ser Gln Tyr Ala Cys Gln Arg Arg Thr Thr
145                 150                 155                 160

Leu Asn Asn Cys Asn His Ile Phe Thr Asp Ala Phe Glu Val Leu Ala
                165                 170                 175

```
Glu Asn Tyr Glu Phe Arg Glu Asn Glu Thr Phe Cys Leu Ala Phe Met
            180                 185                 190

Arg Ala Ala Ser Val Leu Lys Ser Leu Pro Phe Thr Ile Ile Ser Met
        195                 200                 205

Lys Asp Thr Glu Gly Ile Pro Cys Leu Gly Asp Lys Val Lys Cys Val
    210                 215                 220

Ile Glu Glu Ile Ile Glu Asp Gly Ser Ser Glu Val Lys Ala Val
225                 230                 235                 240

Leu Asn Asp Glu Arg Tyr Gln Ser Phe Lys Leu Phe Thr Ser Val Phe
                245                 250                 255

Gly Val Gly Leu Lys Thr Ser Glu Arg Trp Phe Arg Met Gly Phe Arg
            260                 265                 270

Ser Leu Ser Lys Ile Arg Ser Asp Lys Thr Leu Lys Phe Thr Arg Met
        275                 280                 285

Gln Lys Ala Gly Phe Leu Tyr Tyr Glu Asp Leu Val Ser Cys Val Thr
    290                 295                 300

Arg Ala Glu Ala Glu Ala Val Gly Val Leu Val Lys Glu Ala Val Gln
305                 310                 315                 320

Ala Phe Leu Pro Asp Ala Phe Val Thr Met Thr Gly Gly Phe Arg Arg
                325                 330                 335

Gly Lys Lys Met Gly His Asp Val Asp Phe Leu Ile Thr Ser Pro Gly
            340                 345                 350

Ser Thr Asp Asp Glu Glu Gln Gln Leu Leu Pro Lys Val Val Asn Leu
        355                 360                 365

Trp Glu Arg Glu Gly Leu Leu Leu Tyr Cys Asp Leu Val Glu Ser Thr
    370                 375                 380

Leu Glu Lys Ser Lys Leu Pro Ser Arg Asn Val Asp Ala Leu Asp His
385                 390                 395                 400

Phe Gln Lys Cys Phe Leu Ile Leu Lys Leu His His Gln Arg Val Asp
                405                 410                 415

Ser Gly Met Ser Ser Gln Gln Glu Gly Lys Thr Trp Lys Ala Ile Arg
            420                 425                 430

Val Asp Leu Val Met Cys Pro Tyr Glu Leu Arg Ala Phe Ala Leu Leu
        435                 440                 445

Gly Trp Thr Gly Ser Arg Gln Phe Glu Arg Asp Leu Arg Arg Tyr Ala
    450                 455                 460

Thr His Glu Arg Lys Met Ile Leu Asp Asn His Ala Leu Tyr Asp Lys
465                 470                 475                 480

Thr Lys Arg Ile Phe Leu Lys Ala Glu Ser Glu Glu Ile Phe Ala
                485                 490                 495

His Leu Gly Leu Asp Tyr Leu Glu Pro Trp Glu Arg Asn Ala
            500                 505                 510

<210> SEQ ID NO 17
<211> LENGTH: 478
<212> TYPE: PRT
<213> ORGANISM: Artificial Sequence
<220> FEATURE:
<223> OTHER INFORMATION: Pundamilia nyererei AA Seq

<400> SEQUENCE: 17

Met Phe His Thr Pro Ile Val Pro Arg Ala Arg Lys Arg Ser Arg Pro
1               5                   10                  15

Ala Glu Ala Ser Ala Pro Arg Arg Glu Arg Val Lys Phe Glu Asp Val
            20                  25                  30
```

Arg Leu Tyr Leu Val Glu Arg Lys Met Gly Arg Ser Arg Ser Phe
                35                  40                  45

Leu Thr Glu Leu Ala Arg Ser Lys Gly Phe Ile Val Glu Asp Val Leu
 50                  55                  60

Ser Asp Val Val Thr His Val Val Ser Glu Asp Ser Gln Ala Ser Ser
 65                  70                  75                  80

Leu Trp Ala Trp Leu Lys Gly Gly Pro Val Lys Asn Leu Pro Val Met
                 85                  90                  95

His Val Leu Asp Ile Asp Thr Leu Ala Ala Ser Pro Glu Ala Thr Thr
                100                 105                 110

Pro Thr Pro Met Ser Thr Val Ser Gln Tyr Ala Cys Gln Arg Arg Thr
                115                 120                 125

Thr Thr Lys Asn Asn Asn Lys Ile Phe Thr Asp Ala Phe Glu Val Leu
130                 135                 140

Ala Glu Ser His Glu Phe Asn Asp Met Glu Gly Pro Cys Leu Ala Phe
145                 150                 155                 160

Arg Arg Ala Ala Ser Val Leu Lys Ser Leu Pro Trp Thr Val Gln Asn
                165                 170                 175

Leu Arg Val Thr Glu Asp Leu Pro Cys Leu Gly Glu His Ser Met Cys
                180                 185                 190

Val Ile Glu Glu Ile Leu Gln His Gly His Ser Phe Glu Val Glu Lys
                195                 200                 205

Ile Leu Ser Asp Glu Arg Tyr Gln Ile Leu Lys Leu Phe Thr Ser Val
210                 215                 220

Phe Gly Val Gly Pro Lys Thr Ala Glu Lys Trp Tyr Arg Arg Gly Leu
225                 230                 235                 240

Arg Ser Phe Ser Asp Val Leu Ala Glu Pro Asp Ile His Leu Asn Arg
                245                 250                 255

Met Gln Gln Ser Gly Phe Leu His Tyr Gly Asp Ile Ser Arg Ala Val
                260                 265                 270

Ser Lys Ala Glu Ala Gln Ala Leu Gly Asn Ile Ile Asp Glu Ala Val
                275                 280                 285

Arg Ala Ile Thr Pro Asp Ala Ile Leu Thr Leu Thr Gly Gly Phe Arg
                290                 295                 300

Arg Gly Lys Asp Phe Gly His Asp Val Asp Phe Ile Val Thr Thr Pro
305                 310                 315                 320

Gln Leu Gly Lys Glu Glu Arg Leu Leu Thr Ser Val Ile Asp Arg Leu
                325                 330                 335

Lys Gln Gln Gly Ile Leu Leu Tyr Cys Glu Tyr Gln Ala Ser Thr Phe
                340                 345                 350

Asp Glu Ser Lys Leu Pro Ser His Arg Phe Glu Ala Met Asp His Phe
                355                 360                 365

Ala Lys Cys Phe Leu Ile Leu Arg Leu Glu Asp Ser Gln Val Glu Gly
                370                 375                 380

Gly Leu Gln Thr Ala Glu Asp Arg Arg Gly Trp Arg Ala Val Arg
385                 390                 395                 400

Val Asp Leu Val Ser Pro Pro Val Asp Arg Tyr Ala Phe Thr Leu Leu
                405                 410                 415

Gly Trp Ser Gly Ser Arg Gln Phe Glu Arg Asp Leu Arg Arg Phe Ala
                420                 425                 430

Arg Met Glu Arg Arg Met Leu Leu Asp Asn His Ala Leu Tyr Asp Lys
                435                 440                 445

```
Thr Lys Lys Glu Phe Leu Ala Ala Thr Thr Glu Lys Asp Ile Phe Ala
    450                 455                 460
His Leu Gly Leu Glu Tyr Ile Glu Pro Trp Gln Arg Asn Ala
465                 470                 475

<210> SEQ ID NO 18
<211> LENGTH: 8
<212> TYPE: PRT
<213> ORGANISM: Artificial Sequence
<220> FEATURE:
<223> OTHER INFORMATION: Protease cleavage site

<400> SEQUENCE: 18

Met Glu Asn Leu Tyr Phe Gln Gly
1               5
```

MODIFIED TERMINAL DEOXYNUCLEOTIDYL TRANSFERASE (TdT) ENZYMES

REFERENCE TO RELATED APPLICATION

The application claims foreign priority to UK Patent Application No. GB2013086.0, filed on Aug. 21, 2020, the entire contents of which, including any drawings and sequence listing, are incorporated herein by reference.

SEQUENCE LISTING

The instant application contains a Sequence Listing which has been submitted electronically in ASCII format and is hereby incorporated by reference in its entirety. Said ASCII copy, created Jan. 14, 2022, is named 135815-00601_SL.txt and is 63,641 bytes in size.

FIELD OF THE INVENTION

The invention relates to the use of specific terminal deoxynucleotidyl transferase (TdT) enzymes or the homologous amino acid sequence of Polμ, Polβ, Polλ, and Polθ of any species or the homologous amino acid sequence of X family polymerases of any species in a method of nucleic acid synthesis, to methods of synthesizing nucleic acids, and to the use of kits comprising said enzymes in a method of nucleic acid synthesis. The invention also relates to the use of terminal deoxynucleotidyl transferases or homologous enzymes in a method of template independent nucleic acid synthesis.

BACKGROUND OF THE INVENTION

Nucleic acid synthesis is vital to modern biotechnology. The rapid pace of development in the biotechnology arena has been made possible by the scientific community's ability to artificially synthesise DNA, RNA and proteins.

Artificial DNA synthesis allows biotechnology and pharmaceutical companies to develop a range of peptide therapeutics, such as insulin for the treatment of diabetes. It allows researchers to characterise cellular proteins to develop new small molecule therapies for the treatment of diseases our aging population faces today, such as heart disease and cancer. It even paves the way forward to creating life, as the Venter Institute demonstrated in 2010 when they placed an artificially synthesised genome into a bacterial cell.

However, current DNA synthesis technology does not meet the demands of the biotechnology industry. Despite being a mature technology, it is highly challenging to synthesise a DNA strand greater than 200 nucleotides in length in viable yield, and most DNA synthesis companies only offer up to 120 nucleotides routinely. In comparison, an average protein-coding gene is of the order of 2000-3000 contiguous nucleotides, a chromosome is at least a million contiguous nucleotides in length and an average eukaryotic genome numbers in the billions of nucleotides. In order to prepare nucleic acid strands thousands of base pairs in length, all major gene synthesis companies today rely on variations of a 'synthesise and stitch' technique, where overlapping 40-60-mer fragments are synthesised and stitched together by enzymatic copying and extension. Current methods generally allow up to 3 kb in length for routine production.

The reason DNA cannot be synthesised beyond 120-200 nucleotides at a time is due to the current methodology for generating DNA, which uses synthetic chemistry (i.e., phosphoramidite technology) to couple a nucleotide one at a time to make DNA. Even if the efficiency of each nucleotide-coupling step is 99% efficient, it is mathematically impossible to synthesise DNA longer than 200 nucleotides in acceptable yields. The Venter Institute illustrated this laborious process by spending 4 years and 20 million USD to synthesise the relatively small genome of a bacterium.

Known methods of DNA sequencing use template-dependent DNA polymerases to add 3'-reversibly terminated nucleotides to a growing double-stranded substrate. In the 'sequencing-by-synthesis' process, each added nucleotide contains a dye, allowing the user to identify the exact sequence of the template strand. Albeit on double-stranded DNA, this technology is able to produce strands of between 500-1000 bps long. However, this technology is not suitable for de novo nucleic acid synthesis because of the requirement for an existing nucleic acid strand to act as a template.

Various attempts have been made to use a terminal deoxynucleotidyl transferase for de novo single-stranded DNA synthesis. Uncontrolled de novo single-stranded DNA synthesis, as opposed to controlled, takes advantage of TdT's deoxynucleoside 5'-triphosphate (dNTP) 3'-tailing properties on single-stranded DNA to create, for example, homopolymeric adaptor sequences for next-generation sequencing library preparation. In controlled extensions, reversible deoxynucleoside 5'-triphosphate termination technology needs to be employed to prevent uncontrolled addition of dNTPs to the 3'-end of a growing DNA strand. The development of a controlled single-stranded DNA synthesis process through TdT would be invaluable to in situ DNA synthesis for gene assembly or hybridization microarrays as it removes the need for an anhydrous environment and allows the use of various polymers incompatible with organic solvents.

However, TdT has not been shown to efficiently add nucleoside triphosphates containing 3'-O-reversibly terminating moieties for building up a nascent single-stranded DNA chain necessary for a de novo synthesis cycle. A 3'-O-eversible terminating moiety would prevent a terminal transferase like TdT from catalysing the nucleotide transferase reaction between the 3'-end of a growing DNA strand and the 5'-triphosphate of an incoming nucleoside triphosphate.

Applicants and others have previously identified modified terminal deoxynucleotidyl transferases. For example US 2018/023108 A1 (Nuclera), US 2020/002690 A1 (DNA Script), US 2016/108382 A1 (Molecular Assemblies Inc), WO 2018/215803 A1 (Nuclera).

There is therefore a need to identify modified terminal deoxynucleotidyl transferases that readily incorporate 3'-O-reversibly terminated nucleotides. Said modified terminal deoxynucleotidyl transferases can be used to incorporate 3'-O-reversibly terminated nucleotides in a fashion useful for biotechnology and single-stranded DNA synthesis processes in order to provide an improved method of nucleic acid synthesis that is able to overcome the problems associated with currently available methods. The applicants have previously identified novel enzymes in application PCT/GB2020/050247. Described herein are further improved enzymes. The modifications described herein improve the ability to incorporate native nucleotides, particularly dATP.

The enzymes have a higher catalytic activity than the unmodified enzymes and operate at higher temperatures.

BRIEF DESCRIPTION OF THE FIGURES

FIG. 1. Sequence alignment of selected orthologs of wild-type terminal deoxynucleotidyl transferases using the Clustal Omega multiple sequence alignment program provided by the European Molecular Biology Laboratory (EMBL) multiple sequence alignment site. Sequences in order of appearance are SEQ ID NOs: 10-17.

SUMMARY OF THE INVENTION

Figure 2:
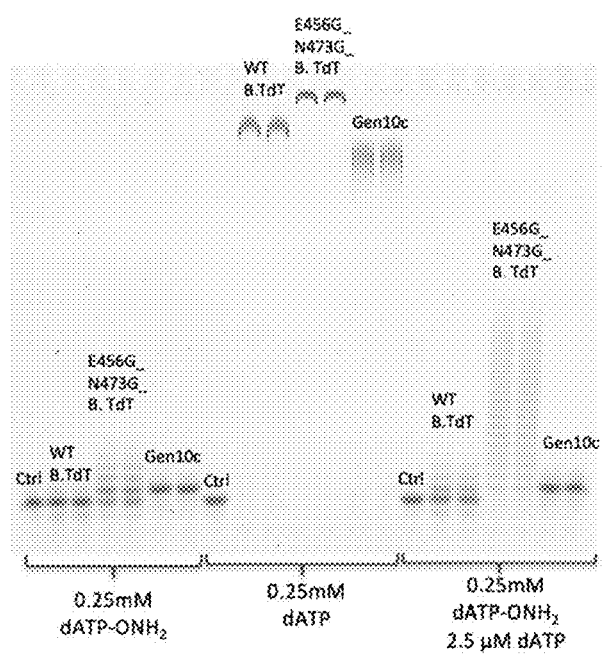
FIG. 2. Tailing experiment (Cacodylate buffer containing 1 mM $CoCl_2$) with enzyme variant (all equimolar)) at 37° C. for 15 min. Wild-type bovine TdT (WT B.TdT), bovine TdT E456G N473G, and GenlOC are compared for their incorporation activity of the dNTPs as indicated on the gel. Terminal transferase activity of TdT variants with the indicated dNTP or dNTPs. dNTP (1 mM) was incubated in a cacodylate buffer supplemented with 1 mM $CoCl_2$, the indicated TdT enzyme variant (1 µM), and yeast inorganic pyrophosphatase at 37° C. for 15 min. Wild-type bovine TdT (WT B.TdT), bovine TdT E456G N473G, and GenlOC are compared for their terminal transferase activity of the indicated dNTPs=. After the 15 min reaction, reactions were killed with stop buffer consisting of sodium hydroxide, EDTA, and 50% v/v formamide. Reactions were directly loaded on a 20% denaturing PAGE gel and imaged by virtue of the 5'-fluorophore on the reacted ssDNA primer.

Described herein are modified terminal deoxynucleotidyl transferase (TdT) enzymes or the homologous amino acid sequence of Polµ, Polβ, Polλ, and Polθ of any species or the homologous amino acid sequence of X family polymerases of any species. Terminal transferase enzymes are ubiquitous in nature and are present in many species. Many known TdT sequences have been reported in the NCBI database www.ncbi.nlm.nih.gov/.

| GI Number | Species www.ncbi.nlm.nih.gov/ |
| --- | --- |
| gi\|768 | *Bos taurus* |
| gi\|460163 | *Gallus gallus* |
| gi\|494987 | *Xenopus laevis* |
| gi\|1354475 | *Oncorhynchus mykiss* |
| gi\|2149634 | *Monodelphis domestica* |
| gi\|12802441 | *Mus musculus* |
| gi\|28852989 | *Ambystoma mexicanum* |
| gi\|38603668 | *Takifugu rubripes* |
| gi\|40037389 | *Raja eglanteria* |
| gi\|40218593 | *Ginglymostoma cirratum* |
| gi\|46369889 | *Danio rerio* |
| gi\|73998101 | *Canis lupus familiaris* |
| gi\|139001476 | *Lemur catta* |
| gi\|139001490 | *Microcebus murinus* |
| gi\|139001511 | *Otolemur garnettii* |
| gi\|148708614 | *Mus musculus* |
| gi\|149040157 | *Rattus norvegicus* |
| gi\|149704611 | *Equus caballus* |
| gi\|164451472 | *Bos taurus* |
| gi\|169642654 | *Xenopus (Silurana) tropicalis* |
| gi\|291394899 | *Oryctolagus cuniculus* |
| gi\|291404551 | *Oryctolagus cuniculus* |
| gi\|301763246 | *Ailuropoda melanoleuca* |
| gi\|311271684 | *Sus scrota* |
| gi\|327280070 | *Anolis carolinensis* |
| gi\|334313404 | *Monodelphis domestica* |
| gi\|344274915 | *Loxodonta africana* |
| gi\|345330196 | *Ornithorhynchus anatinus* |
| gi\|348588114 | *Cavia porcellus* |
| gi\|351697151 | *Heterocephalus glaber* |
| gi\|355562663 | *Macaca mulatta* |
| gi\|395501816 | *Sarcophilus harrisii* |
| gi\|395508711 | *Sarcophilus harrisii* |
| gi\|395850042 | *Otolemur garnettii* |
| gi\|397467153 | *Pan paniscus* |
| gi\|403278452 | *Saimiri boliviensis boliviensis* |
| gi\|410903980 | *Takifugu rubripes* |
| gi\|410975770 | *Felis catus* |
| gi\|432092624 | *Myotis davidii* |
| g\|432113117 | *Myotis davidii* |
| g\|444708211 | *Tupaia chinensis* |
| gi\|1460417122 | *Pleurodeles waltl* |
| g\|466001476 | *Orcinus orca* |
| g\|471358897 | *Trichechus manatus latirostris* |
| gi\|478507321 | *Ceratotherium simum simum* |
| gi\|478528402 | *Ceratotherium simum simum* |
| gi\|488530524 | *Dasypus novemcinctus* |
| gi\|499037612 | *Maylandia zebra* |
| gi\|504135178 | *Ochotona princeps* |
| gi\|505844004 | *Sorex araneus* |
| gi\|505845913 | *Sorex araneus* |
| gi\|507537868 | *Jaculus jaculus* |
| gi\|507572662 | *Jaculus jaculus* |
| gi\|507622751 | *Octodon degus* |
| gi\|507640406 | *Echinops telfairi* |

-continued

| GI Number | Species www.ncbi.nlm.nih.gov/ |
|---|---|
| gi\|507669049 | *Echinops telfairi* |
| gi\|507930719 | *Condylura cristata* |
| gi\|507940587 | *Condylura cristata* |
| gi\|511850623 | *Mustela putorius furo* |
| gi\|512856623 | *Xenopus (Silurana)tropicalis* |
| gi\|512952456 | *Heterocephalus glaber* |
| gi\|524918754 | *Mesocricetus auratus* |
| gi\|527251632 | *Melopsittacus undulatus* |
| gi\|528493137 | *Danio rerio* |
| gi\|528493139 | *Danio rerio* |
| gi\|529438486 | *Falco peregrinus* |
| gi\|530565557 | *Chrysemys picta bellii* |
| gi\|532017142 | *Microtus ochrogaster* |
| gi\|532099471 | *Ictidomys tridecemlineatus* |
| gi\|533166077 | *Chinchilla lanigera* |
| gi\|533189443 | *Chinchilla lanigera* |
| gi\|537205041 | *Cricetulus griseus* |
| gi\|537263119 | *Cricetulus griseus* |
| gi\|543247043 | *Geospiza fortis* |
| gi\|543351492 | *Pseudopodoces humilis* |
| gi\|543731985 | *Columba livia* |
| gi\|544420267 | *Macaca fascicularis* |
| gi\|545193630 | *Equus caballus* |
| gi\|548384565 | *Pundamilia nyererei* |
| gi\|551487466 | *Xiphophorus maculatus* |
| gi\|551523268 | *Xiphophorus maculatus* |
| gi\|554582962 | *Myotis brandtii* |
| gi\|554588252 | *Myotis brandtii* |
| gi\|556778822 | *Pantholops hodgsonii* |
| gi\|556990133 | *Latimeria chalumnae* |
| gi\|557297894 | *Alligator sinensis* |
| gi\|558116760 | *Pelodiscus sinensis* |
| gi\|558207237 | *Myotis lucifugus* |
| gi\|560895997 | *Camelus ferus* |
| gi\|560897502 | *Camelus ferus* |
| gi\|562857949 | *Tupaia chinensis* |
| gi\|562876575 | *Tupaia chinensis* |
| gi\|564229057 | *Alligator mississippiensis* |
| gi\|564236372 | *Alligator mississippiensis* |
| gi\|564384286 | *Rattus norvegicus* |
| gi\|573884994 | *Lepisosteus oculatus* |
| gi\|63054850 | *Homo sapiens* [isoform 1] |
| gi\|63054852 | *Homo sapiens* [isoform 2] |

Figure 1:
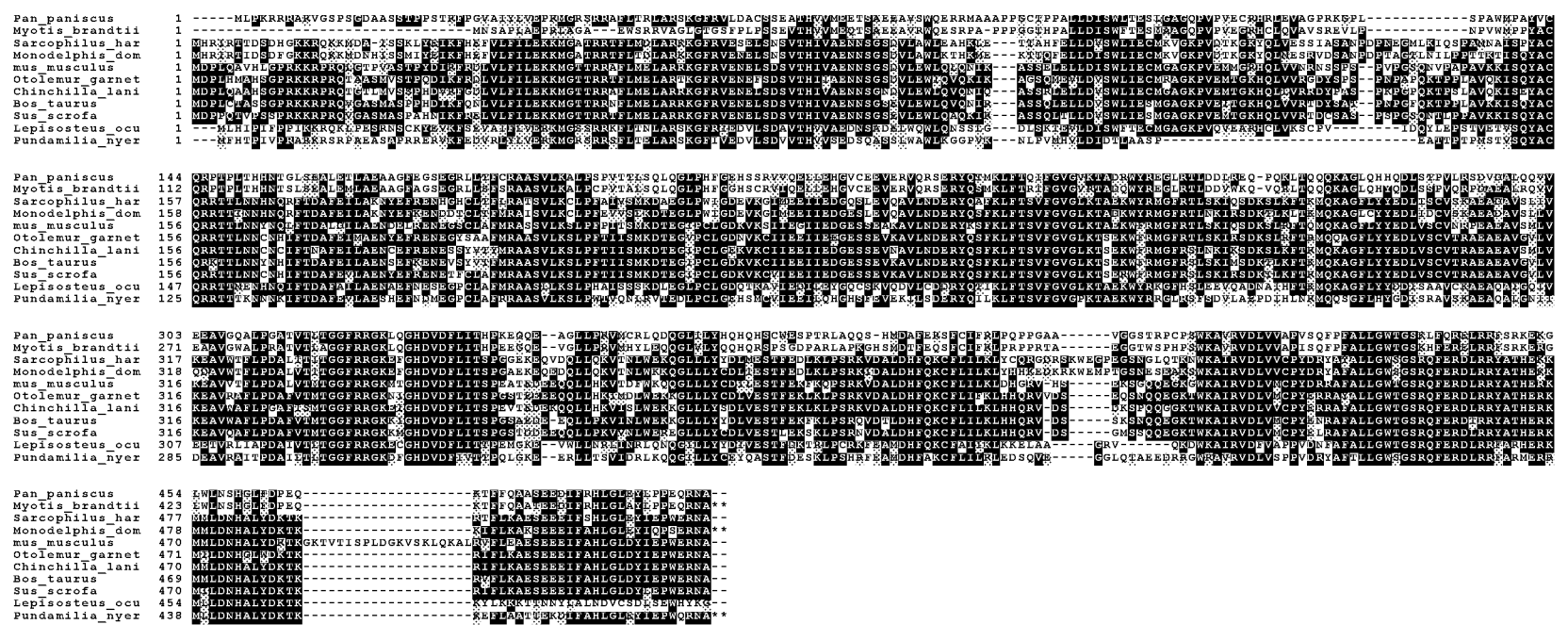

The sequences of the various described terminal transferases show some regions of highly conserved sequence, and some regions which are highly diverse between different species. A sequence alignment for sequences from a selection of species is shown in FIG. 1.

The inventors have modified the terminal transferase from Bos Taurus (shown as SEQ ID NO: 1). However the corresponding modifications can be introduced into the analogous or homologous terminal transferases from any other species, including the sequences listed above in the various NCBI entries, including those shown in FIG. 2 or truncated versions thereof.

The amino acid sequence of Bos Taurus is shown below (SEQ ID NO: 1)

MDPLCTASSGPRKKRPRQVGASMASPPHDIKFQNLVLFILEKKMGTTRR

NFLMELARRKGFRVENELSDSVTHIVAENNSGSEVLEWLQVQNIRASSQ

LELLDVSWLIESMGAGKPVEITGKHQLVVRTDYSATPNPGFQKTPPLAV

KKISQYACQRKTTLNNYNHIFTDAFEILAENSEFKENEVSYVTFMRAAS

VLKSLPFTIISMKDTEGIPCLGDKVKCIIEEIIEDGESSEVKAVLNDER

YQSFKLFTSVEGVGLKTSEKWERMGERSLSKIMSDKTLKFTKMQKAGFL

YYEDLVSCVTRAEAEAVGVLVKEAVWAFLPDAFVTMTGGFRRGKKIGHD

VDFLITSPGSAEDEEQLLPKVINLWEKKGLLLYYDLVESTFEKFKLPSR

QVDTLDHFQKCFLILKLHHQRVDSSKSNQQEGKTWKAIRVDLVMCPYEN

RAFALLGWTGSRQFERDIRRYATHERKMMLDNHALYDKTKRVFLKAESE

EEIFAHLGLDYIEPWERNA

All amino acid numbering is in reference to SEQ ID NO: 1, the full length sequence of 509 amino acids. Applicants use truncations of the full length sequence which retain activity, and thus the truncations, being fewer amino acids, will have different numbering.

The inventors have identified various amino acids modifications in the amino acid sequence having improved properties. The modifications described herein improve the ability to incorporate native nucleotides, particularly dATP. The enzymes have a higher catalytic activity than the unmodified enzymes and operate at higher temperatures.

Described herein are modified terminal deoxynucleotidyl transferase (TdT) enzymes comprising amino acid modifications when compared to a wild type sequence SEQ ID NO: 1 or a truncated version thereof or the homologous amino acid sequence of a terminal deoxynucleotidyl transferase (TdT) enzyme in other species or the homologous amino acid sequence of Polμ, Polβ, Polλ, and Polθ of any species or the homologous amino acid sequence of X family polymerases of any species.

Amino acid locations having improved activity include R193, E456, R457, or N473.

Described is a modified terminal deoxynucleotidyl transferase (TdT) enzyme wherein the modification is at R193.

Described is a modified terminal deoxynucleotidyl transferase (TdT) enzyme wherein the modification is at E456.

Described is a modified terminal deoxynucleotidyl transferase (TdT) enzyme wherein the modification is at R457.

Described is a modified terminal deoxynucleotidyl transferase (TdT) enzyme wherein the modification is at N473.

Described is a modified terminal deoxynucleotidyl transferase (TdT) enzyme wherein the amino acid modifications are selected from
  a. R193 and/or
  b. Two or more of the amino acid positions E456, R457 and/or N473.

Described is a modified terminal deoxynucleotidyl transferase (TdT) enzyme wherein modifications are at the three amino acid positions E456, R457, and N473.

Described is a modified terminal deoxynucleotidyl transferase (TdT) enzyme wherein modifications are at the three amino acid positions R193, E456, N473.

Described is a modified terminal deoxynucleotidyl transferase (TdT) enzyme wherein modifications are at the four amino acid positions R193, E456, R457, and N473.

Modifications include one or more of R193H, E456G, R457S, and/or N473G. Modifications include R193H, E456G, R457S, and N473G. Modifications include any combination of the above mutations. Modifications include both E456G and N473G. Modifications include E456G, R457S, and N473G. Modifications which improve the incorporation of nucleotides can be at one or more of the selected positions shown below (SEQ ID NO: 2).

MDPLCTASSGPRKKRPRQVGASMASPPHDIKFQNLVLFILEKKMGTTRR

NFLMELARRKGFRVENELSDSVTHIVAENNSGSEVLEWLQVQNIRASSQ

-continued

LELLDVSWLIESMGAGKPVEITGKHQLVVRTDYSATPNPGFQKTPPLAV

KKISQYACQRKTTLNNYNHIFTDAFEILAENSEFKENEVSYVTFMRAAS

VLKSLPFTIISMKDTEGIPCLGDKVKCIIEEIIEDGESSEVKAVLNDER

YQSFKLFTSVEGVGLKTSEKWERMGERSLSKIMSDKTLKFTKMQKAGFL

YYEDLVSCVTRAEAEAVGVLVKEAVWAFLPDAFVTMTGGFRRGKKIGHD

VDFLITSPGSAEDEEQLLPKVINLWEKKGLLLYYDLVESTFEKFKLPSR

QVDTLDHFQKCFLILKLHHQRVDSSKSNQQEGKTWKAIRVDLVMCPYEN

RAFALLGWTGSRQFERDIRRYATHERKMMLDNHALYDKTKRVFLKAESE

EEIFAHLGLDYIEPWERNA

References to particular sequences include truncations thereof. Included herein are modified terminal deoxynucleotidyl transferase (TdT) enzyme comprising at least one amino acid modification when compared to a wild type sequence SEQ ID NO: 1 or a truncated version thereof, or the homologous amino acid sequence of a terminal deoxynucleotidyl transferase (TdT) enzyme in other species, wherein the modification is selected from one or more of the amino acid of the sequence of SEQ ID NO: 1 or the homologous regions in other species.

Truncated proteins may include at least the region shown below including one or more of the relevant modifications (SEQ ID NO: 3).

KISQYACQRKTTLNNYNHIFTDAFEILAENSEFKENEVSYVTFMRAASV

LKSLPFTIISMKDTEGIPCLGDKVKCIIEEIIEDGESSEVKAVLNDERY

QSFKLFTSVEGVGLKTSEKWERMGERSLSKIMSDKTLKFTKMQKAGFLY

YEDLVSCVTRAEAEAVGVLVKEAVWAFLPDAFVTMTGGFRRGKKIGHDV

DFLITSPGSAEDEEQLLPKVINLWEKKGLLLYYDLVESTFEKFKLPSRQ

VDTLDHFQKCFLILKLHHQRVDSSKSNQQEGKTWKAIRVDLVMCPYENR

AFALLGWTGSRQFERDIRRYATHERKMMLDNHALYDKTKRVFLKAESEE

EIFAHLGLDYIEPWERNA

Described herein is a modified terminal deoxynucleotidyl transferase (TdT) enzyme comprising at least the SEQ ID NO: 3:

KISQYACQRKTTLNNYNHIFTDAFEILAENSEFKENEVSYVTFMRAASV

LKSLPFTIISMKDTEGIPCLGDKVKCIIEEIIEDGESSEVKAVLNDERY

QSFKLFTSVEGVGLKTSEKWERMGERSLSKIMSDKTLKFTKMQKAGFLY

YEDLVSCVTRAEAEAVGVLVKEAVWAFLPDAFVTMTGGFRRGKKIGHDV

DFLITSPGSAEDEEQLLPKVINLWEKKGLLLYYDLVESTFEKFKLPSRQ

VDTLDHFQKCFLILKLHHQRVDSSKSNQQEGKTWKAIRVDLVMCPYENR

AFALLGWTGSRQFERDIRRYATHERKMMLDNHALYDKTKRVFLKAESEE

EIFAHLGLDYIEPWERNA or the homologous regions in other species, wherein the sequence has one or more amino acid modifications in one or more of the amino acid positions R193, E456, R457, and/or N473 of the full length sequence.

Homologous refers to protein sequences between two or more proteins that possess a common evolutionary origin, including proteins from superfamilies in the same species of organism as well as homologous proteins from different species. Such proteins (and their encoding nucleic acids) have sequence homology, as reflected by their sequence similarity, whether in terms of percent identity or by the presence of specific residues or motifs and conserved positions. A variety of protein (and their encoding nucleic acid) sequence alignment tools may be used to determine sequence homology. For example, the Clustal Omega multiple sequence alignment program provided by the European Molecular Biology Laboratory (EMBL) can be used to determine sequence homology or homologous regions.

Improved sequences as described herein can contain two or more of the aforementioned modifications, namely, for example, a. a first modification at position E456 of the sequence of SEQ ID NO: 1 or the homologous region in other species; and b. a second modification at position N473 of the sequence of SEQ ID NO: 1 or the homologous regions in other species or a truncated sequence.

or a. a first modification at position E456 of the sequence of SEQ ID NO: 1 or the homologous region in other species; and b. a second modification at position R457 of the sequence of SEQ ID NO: 1 or the homologous region in other species; and c. a third modification at position N473 of the sequence of SEQ ID NO: 1 or the homologous regions in other species or a truncated sequence.

or a. a first modification at position R193 of the sequence of SEQ ID NO: 1 or the homologous region in other species; and b. a second modification at position E456 of the sequence of SEQ ID NO: 1 or the homologous region in other species; and c. a third modification at position R457 of the sequence of SEQ ID NO: 1 or the homologous region in other species; and d. a fourth modification at position N473 of the sequence of SEQ ID NO: 1 or the homologous regions in other species or a truncated sequence.

As a comparison with other species, the sequence of *Lepisosteus oculatus* (spotted gar) TdT is shown below (SEQ ID NO: 4):

MLHIPIFPPIKKRQKLPESRNSCKYEVKFSEVAIFLVERKMGSSRRKFL

TNLARSKGFRIEDVLSDAVTHVVAEDNSADELWQWLQNSSLGDLSKIEV

LDISWFTECMGAGKPVQVEARHCLVKSCPVIDQYLEPSTVETVSQYACQ

RRTTMENHNQIFTDAFAILAENAEFNESEGPCLAFMRAASLLKSLPHAI

SSSKDLEGLPCLGDQTKAVIEDILEYGQCSKVQDVLCDDRYQTIKLFTS

VFGVGLKTAEKWYRKGFHSLEEVQADNAIHFTKMQKAGFLYYDDISAAV

CKAEAQAIGQIVEETVRLIAPDAIVTLTGGFRRGKECGHDVDFLITTPE

MGKEVWLLNRLINRLQNQGILLYYDIVESTFDKTRLPCRKFEAMDHFQK

CFAIIKLKKELAAGRVQKDWKAIRVDFVAPPVDNFAFALLGWTGSRQFE

RDLRRFARHERKMLLDNHALYDKTKKIFLPAKTEEDIFAHLGLDYIDPW

QRNA

The amino acid positions are highlighted below (SEQ ID NO: 4)

MLHIPIFPPIKKRQKLPESRNSCKYEVKFSEVAIPLVERKMGSSRRKFL

TNLARSKGFRIEDVLSDAVTHVVAEDNSADELWQWLQNSSLGDLSKIEV

LDISWFTECMGAGKPVQVEARHCLVKSCPVIDQYLEPSTVETVSQYACQ

RRTTMENHNQIFTDAFAILAENAEFNESEGPCLAFMRAASLLKSLPHAI

SSSKDLEGLPCLGDQTKAVIEDILEYGQCSKVQDVLCDDRYQTIKLFTS

VFGVGLKTAEKWYRKGFHSLEEVQADNAIHFTKMQKAGFLYYDDISAAV

CKAEAQAIGQIVEETVRLIAPDAIVTLTGGFRRGKECGHDVDFLITTPE

MGKEVWLLNRLINRLQNQGILLYYDIVESTFDKTRLPCRKFEAMDHFQK

CFAIIKLKKELAAGRVQKDWKAIRVDFVAPPVDNFAFALLGWTGSRQFE

RDLRRFARHERKMLLDNHALYDKTKKIFLPAKTEEDIFAHLGLDYIDPW

QRNA

The amino acid sequence of truncated *Lepisosteus oculatus* TdT is shown below (SEQ ID NO: 5):

TVSQYACQRRTTMENHNQIFTDAFAILAENAEFNESEGPCLAFMRAASLL

KSLPHAISSSKDLEGLPCLGDQTKAVIEDILEYGQCSKVQDVLCDDRYQT

IKLFTSVEGVGLKTAEKWYRKGEHSLEEVQADNAIHFTKMQKAGFLYYDD

ISAAVCKAEAQAIGQIVEETVRLIAPDAIVTLIGGERRGKECGHDVDFLI

TTPEMGKEVWLLNRLINRLQNQGILLYYDIVESTEDKTRLPCRKFEAMDH

FQKCFAIIKLKKELAAGRVQKDWKAIRVDEVAPPVDNFAFALLGWIGSRQ

FERDLRRFARHERKMLLDNHALYDKIKKIFLPAKTEEDIFAHLGLDYIDP

WQRNA wherein the sequence has one or more amino acid modifications in one or more of the amino acid positions R193, E441, E442, and/or N458 of the full length sequence. The aforementioned positions or homologous to full length Bos taurus TdT amino acid positions R193, E456, R457, and N473, respectively.

As a comparison with other species, the sequence of *Mus musculus* (mouse) TdT is shown below (SEQ ID NO: 6):

MDPLQAVHLGPRKKRPRQLGTPVASTPYDIRFRDLVLFILEKKMGTTRRA

FLMELARRKGFRVENELSDSVTHIVAENNSGSDVLEWLQLQNIKASSELE

LLDISWLIECMGAGKPVEMMGRHQLVVNRNSSPSPVPGSQNVPAPAVKKI

SQYACQRRTTLNNYNQLFTDALDILAENDELRENEGSCLAFMRASSVLKS

LPFPITSMKDTEGIPCLGDKVKSIIEGIIEDGESSEAKAVLNDERYKSFK

LFTSVFGVGLKTAEKWFRMGFRTLSKIQSDKSLRFTQMQKAGFLYYEDLV

SCVNRPEAEAVSMLVKEAVVTFLPDALVTMTGGFRRGKMTGHDVDFLITS

PEATEDEEQQLLHKVTDFWKQQGLLLYCDILESTFEKFKQPSRKVDALDH

FQKCFLILKLDHGRVHSEKSGQQEGKGWKAIRVDLVMCPYDRRAFALLGW

TGSRQFERDLRRYATHERKMMLDNHALYDRTKGKTVTISPLDGKVSKLQK

ALRVFLEAESEEEIFAHLGLDYIEPWERNA

Modifications which improve the incorporation of modified nucleotides can be at one or more of selected positions shown below (SEQ ID NO: 6).

MDPLQAVHLGPRKKRPRQLGTPVASTPYDIRFRDLVLFILEKKMGTTRR

AFLMELARRKGFRVENELSDSVTHIVAENNSGSDVLEWLQLQNIKASSE

LELLDISWLIECMGAGKPVEMMGRHQLVVNRNSSPSPVPGSQNVPAPAV

KKISQYACQRRTTLNNYNQLFTDALDILAENDELRENEGSCLAFMRASS

VLKSLPFPITSMKDTEGIPCLGDKVKSIIEGIIEDGESSEAKAVLNDER

YKSFKLFTSVFGVGLKTAEKWFRMGFRTLSKIQSDKSLRFTQMQKAGFL

YYEDLVSCVNRPEAEAVSMLVKEAVVTFLPDALVTMTGGFRRGKMTGHD

VDFLITSPEATEDEEQQLLHKVTDFWKQQGLLLYCDILESTFEKFKQPS

RKVDALDHFQKCFLILKLDHGRVHSEKSGQQEGKGWKAIRVDLVMCPYD

RRAFALLGWTGSRQFERDLRRYATHERKMMLDNHALYDRTKGKTVTISP

LDGKVSKLQKALRVFLEAESEEEIFAHLGLDYIEPWERNA

Thus by a process of aligning sequences, it is immediately apparent which regions in the sequences of terminal transferases from other species correspond to the sequences described herein with respect to the bovine sequence shown in SEQ ID NO: 1.

Sequence homology extends to all modified or wild-type members of family X polymerases, such as DNA Polμ (also known as DNA polymerase mu or POLM), DNA Polβ (also known as DNA polymerase beta or POLB), and DNA Polλ (also known known as DNA polymerase lambda or POLL). It is well known in the art that all family X member polymerases, of which TdT is a member, either have terminal transferase activity or can be engineered to gain terminal transferase activity akin to terminal deoxynucleotidyl transferase (Biochim Biophys Acta. 2010 May; 1804(5): 1136-1150). For example, when the following human TdT loop1 amino acid sequence (SEQ ID NO: 7)

...ESTFEKLRLPSRKVDALDHF...

was engineered to replace the following human Polμ amino acid residues (SEQ ID NO: 8)

...HSCCESPTRLAQQSHMDAF..., the chimeric human Polμ containing human TdT loop1 gained robust terminal transferase activity (Nucleic Acids Res. 2006 September; 34(16): 4572-4582).

Furthermore, it was generally demonstrated in US patent application no. 2019/0078065 that family X polymerases when engineered to contain TdT loop1 chimeras could gain robust terminal transferase activity. Additionally, it was demonstrated that TdT could be converted into a template-dependent polymerase through specific mutations in the loop1 motif (Nucleic Acids Research, June 2009, 37(14): 4642-4656). As it has been shown in the art, family X polymerases can be trivially modified to either display template-dependent or template-independent nucleotidyl transferase activities. Therefore, all motifs, regions, and mutations demonstrated in this patent can be trivially extended to modified X family polymerases to enable modified X family polymerases to incorporate 3'-modified nucleotides, reversibly terminated nucleotides, and modified nucleotides in general to effect methods of nucleic acid synthesis.

As a comparison with other family X polymerases, the human Polµ sequence is shown below (SEQ ID NO: 9):

MLPKRRRARVGSPSGDAASSTPPSTRFPGVAIYLVEPRMGRSRRAFLTG

LARSKGFRVLDACSSEATHVVMEETSAEEAVSWQERRMAAAPPGCTPPA

LLDISWLTESLGAGQPVPVECRHRLEVAGPRKGPLSPAWMPAYACQRPT

PLTHHNTGLSEALEILAEAAGFEGSEGRLLTFCRAASVLKALPSPVTTL

SQLQGLPHFGEHSSRVVQELLEHGVCEEVERVRRSERYQTMKLFTQIFG

VGVKTADRWYREGLRTLDDLREQPQKLTQQQKAGLQHHQDLSTPVLRSD

VDALQQVVEEAVGQALPGATVTLIGGERRGKLQGHDVDFLITHPKEGQE

AGLLPRVMCRLQDQGLILYHQHQHSCCESPTRLAQQSHMDAFERSFCIF

RLPQPPGAAVGGSTRPCPSWKAVRVDLVVAPVSQFPFALLGWTGSKLFQ

RELRRFSRKEKGLWLNSHGLFDPEQKTFFQAASEEDIFRHLGLEYLPPE

QRNA

Thus by a process of aligning sequences, it is immediately apparent which positions in the sequences of all family X polymerases from any species correspond to the sequences described herein with respect to the bovine sequence shown in SEQ ID NO: 1.

Furthermore, the A family polymerase, DNA Polθ (also known as DNA polymerase theta or POLQ) was demonstrated to display robust terminal transferase capability (eLife. 2016; 5: e13740). DNA Polθ was also demonstrated to be useful in methods of nucleic acid synthesis (GB patent application no. 2553274). In US patent application no. 2019/0078065, it was demonstrated that chimeras of DNA Polθ and family X polymerases could be engineered to gain robust terminal transferase activity and become competent for methods of nucleic acid synthesis. Therefore, all motifs, regions, and mutations demonstrated in this patent can be trivially extended to modified A family polymerases, especially DNA Polθ, to enable modified A family polymerases.

DETAILED DESCRIPTION OF THE INVENTION

Figure 3:
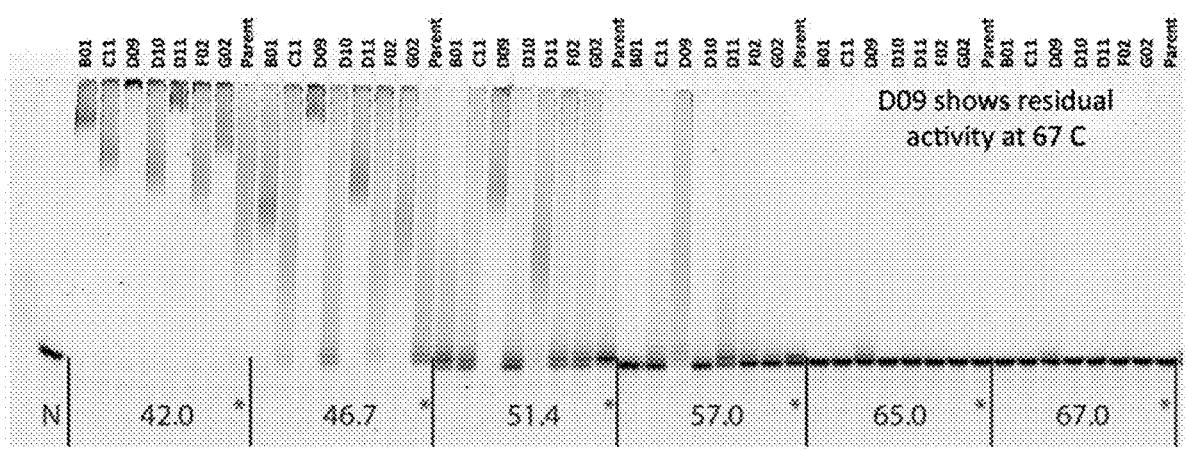
FIG. 3. dATP (1 mM dATP) tailing experiment (1×Cut-Smart buffer+1 mM $CoCl_2$) with enzyme variant (3 µM) at indicated temperature (° C.) for 15 min. D09 is Gar R3-F1 TSA Variant 1 and D11 is Gar R3-F1 TSA Variant 2. Terminal transferase activity of TdT variants with dATP. dATP (1 mM) was incubated in 1×CutSmart buffer supplemented with 1 mM $CoCl_2$, the indicated TdT enzyme variant (3 µM), and 0.05 µl thermostable inorganic pyrophosphatase (New England Biolabs, 2,000 units/ml stock) at the indicated temperature (° C.) for 15 min. D09 is Gar R3-F1 TSA Variant 1 and D11 is Gar R3-F1 TSA Variant 2. Reactions were first pre-incubated at the specified temperature for 5 min with all of the reaction components assembled except dATP; dATP was added to initiate the reaction. After the 10 min reaction, reactions were killed with stop buffer consisting of sodium hydroxide, EDTA, and 50% v/v formamide. Reactions were directly loaded on a 20% denaturing PAGE gel and imaged by virtue of the 5'-fluorophore on the reacted ssDNA primer.
Figure 4:
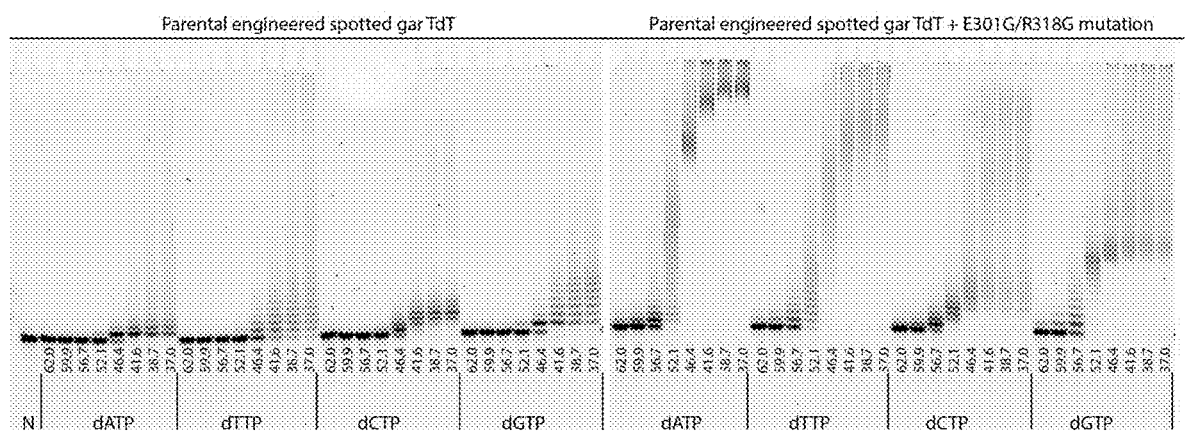
FIG. 4. The dNTP terminal transferase capability of R3-F1 TdT parent (left gel, SEQ 6.1) was compared to R3-F1 TdT TSA variant 1 (right gel, SEQ 6.2). Reactions were incubated for 10 min at the specified temperature (° C.) indicated on the figure with a 5'-fluorophore labelled single-stranded DNA primer (0.1 µM) in 1×CutSmart buffer (New England Biolabs), 1 mM $CoCl_2$, 0.5 mM indicated dNTP on the figure, 0.05 µl thermostable inorganic pyrophosphatase (New England Biolabs, 2,000 units/ml stock). Reactions were first pre-incubated at the specified temperature for 5 min with all of the reaction components assembled except the indicated dNTP; the indicated dNTP was added to initiate the reaction. After the 10 min reaction, reactions were killed with stop buffer consisting of sodium hydroxide, EDTA, and 50% v/v formamide. Reactions were directly loaded on a 20% denaturing PAGE gel and imaged by virtue of the 5'-fluorophore on the reacted ssDNA primer. From FIG. 4, it is clear that the 6.2 Gar R3-F1 TSA mutant 1 (bovine E456G/N473G) convey both thermostability and enhanced terminal transferase activity at all temperatures tested when compared to the 6.1 Gar R3-F1 parent. The 6.1 Gar TdT, like WT TdTs, disfavors dATP tailing as indicated by the shorter tail lengths in FIG. 4 compared with the other dNTPs. Remarkably, the 6.2 Gar R3-F1 TSA mutant 1 demonstrates a drastic increase in terminal transferase activity for dATP; indeed, 6.2 demonstrates higher activity for dATP than any other dNTP.

The inventors have evolved for a TdT enzyme that will tail canonical dATP at temperatures higher than 37° C. They obtained a group of candidates that tail significantly more than the parent at 37° C. and higher, with one candidate showing residual activity at 67° C. (FIG. 3). Inventors have shown that the modifications can be applied to enzyme sequences from varying species.

The enzymes described herein have a greater catalytic efficiency and utilise nucleotide reagents at a lower concentration than wild type sequences.

Where used in conjunction with terminated nucleotide reagents, enzymes having a high efficiency for incorporation of native nucleotides without a terminator modification can be used to deplete the concentration of native reagents and improve the efficiency of nucleic acid synthesis.

Described herein are modified terminal deoxynucleotidyl transferase (TdT) enzymes. The enzymes have an improved catalytic efficiency for nucleotide incorporation. Terminal transferase enzymes are ubiquitous in nature and are present in many species. Many known TdT sequences have been reported in the NCBI database. The sequences described herein are modified from the sequence of the cow, but the corresponding changes can be introduced into the homologous sequences from other species. Homologous amino acid sequences of Polµ, Polβ, Polλ, and Polθ or the homologous amino acid sequence of X family polymerases also possess terminal transferase activity. References to terminal transferase also include homologous amino acid sequences of Polµ, Polβ, Polλ, and Polθ or the homologous amino acid sequence of X family polymerases where such sequences possess terminal transferase activity.

Disclosed herein is a modified terminal deoxynucleotidyl transferase (TdT) enzyme comprising at least one amino acid modification when compared to a wild type sequence, wherein the modification is selected from one or more of the amino acid positions of the sequence of SEQ ID NO: 1 or the homologous regions in other species or a truncated portion thereof.

Described herein is a modified terminal deoxynucleotidyl transferase (TdT) enzyme comprising at least the SEQ ID NO: 3:

KISQYACQRKTTLNNYNHIFTDAFEILAENSEFKENEVSYVTFMRAASV

LKSLPFTIISMKDTEGIPCLGDKVKCIIEEIIEDGESSEVKAVLNDERY

QSFKLFTSVFGVGLKTSEKWFRMGFRSLSKIMSDKTLKFTKMQKAGFLY

YEDLVSCVTRAEAEAVGVLVKEAVWAFLPDAFVTMTGGFRRGKKIGHDV

DFLITSPGSAEDEEQLLPKVINLWEKKGLLLYYDLVESTFEKFKLPSRQ

VDTLDHFQKCFLILKLHHQRVDSSKSNQQEGKTWKAIRVDLVMCPYENR

AFALLGWTGSRQFERDIRRYATHERKMMLDNHALYDKTKRVFLKAESEE

EIFAHLGLDYIEPWERNA or the equivalent homologous region in other species, wherein the sequence has one or more amino acid modifications in one or more of the amino acid positions E456 or N473 of the full length sequence. The sequence above of 355 amino acids can be attached to other amino acids without affecting the function of the enzyme. For example there can be a further N-terminal sequence that is incorporated simply as a protease cleavage site, for example the sequence MENLYFQG (SEQ ID NO: 18).

Further disclosed is a modified terminal deoxynucleotidyl transferase (TdT) enzyme comprising at least two amino acid modifications when compared to a wild type sequence SEQ ID NO: 1 or the homologous amino acid sequence of a terminal deoxynucleotidyl transferase (TdT) enzyme in other species, wherein the modifications are selected from modifications at the amino acid positions E456 and N473 of the sequence of SEQ ID NO: 1 or the homologous region in other species.

The modifications can be chosen from any amino acid that differs from the wild type sequence. The amino acid can be a naturally occurring amino acid. The modified amino acid can be selected from ala, arg, asn, asp, cys, gln, glu, gly, his, ile, leu, lys, met, phe, pro, ser, thr, trp, val, and sec.

For the purposes of brevity, the modifications are further described in relation to SEQ ID NO: 1, but the modifications are applicable to the sequences from other species, for example those sequences listed above having sequences in the NCBI database. The sequence modifications also apply to truncated versions of SEQ ID NO: 1.

The sequences can be modified at positions in addition to those regions described. Embodiments on the invention may include for example sequences having modifications to amino acids outside the defined positions, providing those sequences retain terminal transferase activity. Embodiments of the invention may include for example sequences having truncations of amino acids outside the defined positions, providing those sequences retain terminal transferase activity. For example the sequences may be BRCT truncated as described in application WO2018215803 where amino acids are removed from the N-terminus whilst retaining or improving activity. Alterations, additions, insertions or deletions or truncations to amino acid positions outside the claimed regions are therefore within the scope of the invention, providing that the claimed regions as defined are modified as claimed. The sequences described herein refer to TdT enzymes, which are typically at least 300 amino acids in length. All sequences described herein can be seen as having at least 300 amino acids. The claims do not cover peptide fragments or sequences which do not function as terminal transferase enzymes.

Modifications disclosed herein contain at least one modification at the defined positions. In certain locations, mutations can be preferentially combined.

Specific amino acid changes can include any one of E456G and N473G. Specific amino acid changes can include both of E456G and N473G.

Specific amino acid changes can include
a. R193H and/or
b. Two or more of the amino acid positions E456G, R457S and/or N473G.

Specific amino acid changes can include R193H, E456G, R457S and N473G.

Also disclosed is a method of nucleic acid synthesis, which comprises the steps of:
(a) providing an initiator oligonucleotide; and
(b) adding a nucleotide to said initiator oligonucleotide in the presence of a terminal deoxynucleotidyl transferase (TdT) as defined herein.

The method can add greater than 1 nucleotide. The nucleotides are not blocked at the 3'-position.

The enzymes can preferentially incorporate one of the four nucleotides. Terminal transferases typically do not incorporate dATP as efficiently as other nucleotides, such as dGTP, dTTP, and dCTP (Basu et al., Synthesis of Compositionally Unique DNA By Terminal Deoxynucleotidyl Transferase Biochem. Biophys. Res. Commun., 1983). Modifications described herein convey both thermostability and enhanced terminal transferase activity at all temperatures tested when compared to the parent. Remarkably, the enzymes demonstrate a drastic increase in terminal transferase activity for dATP; indeed they demonstrate higher activity for dATP than any other dNTP.

The enzymes are especially well suited to terminator-free enzymatic DNA synthesis for de novo template-independent nucleic acid synthesis. Methods of terminator-free enzymatic DNA synthesis control include pH control such as that described in U.S. Provisional Application No. 62/333,501; apyrase control such as that described in U.S. Provisional Application No. 62/575,017; reduced activity control such as that described in U.S. Provisional Application No. 62/741,143; caging control of necessary co-factors such as that described in bioRxiv doi 10.1101/2020.02.19.956888; dNTP concentration, reaction time, and dNTP ratio control such as that described in U.S. Provisional Application No. 62/513,111; and tethered nucleoside triphosphate control such as that described in U.S. Provisional Application No. 62/354,635.

The enzyme can also be used to remove nucleotides containing a 3'-OH moiety in a solution of nucleotides containing a 3'-block or 3'-reversible block or 3'-terminator moiety as the enzyme will preferentially incorporate 3'-OH nucleotides onto the 3'-end of a single-stranded DNA molecule.

The enzyme can also be used for other molecular biology applications, including the TUNEL assay for identifying and quantifying apoptotic cells.

References herein to 'nucleoside triphosphates' refer to a molecule containing a nucleoside (i.e. a base attached to a deoxyribose or ribose sugar molecule) bound to three phosphate groups. Examples of nucleoside triphosphates that contain deoxyribose are: deoxyadenosine triphosphate (dATP), deoxyguanosine triphosphate (dGTP), deoxycytidine triphosphate (dCTP) or deoxythymidine triphosphate (dTTP). Examples of nucleoside triphosphates that contain ribose are: adenosine triphosphate (ATP), guanosine triphosphate (GTP), cytidine triphosphate (CTP) or uridine triphosphate (UTP). Other types of nucleosides may be bound to three phosphates to form nucleoside triphosphates, such as naturally occurring modified nucleosides and artificial nucleosides.

References herein to an 'initiator oligonucleotide' or 'initiator sequence' refer to a short oligonucleotide with a free 3'-end which the nucleotide can be attached to. In one embodiment, the initiator sequence is a DNA initiator sequence. In an alternative embodiment, the initiator sequence is an RNA initiator sequence.

References herein to a 'DNA initiator sequence' refer to a small sequence of DNA which the nucleotide can be attached to, i.e., DNA will be synthesised from the end of the DNA initiator sequence.

In one embodiment, the initiator sequence is between 5 and 50 nucleotides long, such as between 5 and 30 nucleotides long (i.e. between 10 and 30), in particular between 5 and 20 nucleotides long (i.e., approximately 20 nucleotides long), more particularly 5 to 15 nucleotides long, for example 10 to 15 nucleotides long, especially 12 nucleotides long.

In one embodiment, the initiator sequence is single-stranded. In an alternative embodiment, the initiator sequence is double-stranded. It will be understood by persons skilled in the art that a 3'-overhang (i.e., a free 3'-end) allows for efficient addition.

In one embodiment, the initiator sequence is immobilised on a solid support. This allows TdT and the cleaving agent to be removed (in steps (c) and (e), respectively) without washing away the synthesised nucleic acid. The initiator sequence may be attached to a solid support stable under aqueous conditions so that the method can be easily performed via a flow setup.

In one embodiment, the initiator sequence is immobilised on a solid support via a reversible interacting moiety, such as a chemically-cleavable linker, an antibody/immunogenic epitope, a biotin/biotin binding protein (such as avidin or streptavidin), or glutathione-GST tag. Therefore, in a further embodiment, the method additionally comprises extracting the resultant nucleic acid by removing the reversible interacting moiety in the initiator sequence, such as by incubating with proteinase K.

In one embodiment, the initiator sequence contains a base or base sequence recognisable by an enzyme. A base recognised by an enzyme, such as a glycosylase, may be removed to generate an abasic site which may be cleaved by chemical or enzymatic means. A base sequence may be recognised and cleaved by a restriction enzyme. The initiator may contain a uracil or 8-oxoguanine nucleobase.

In a further embodiment, the initiator sequence is immobilised on a solid support via a chemically-cleavable linker, such as a disulfide, allyl, or azide-masked hemiaminal ether linker. Therefore, in one embodiment, the method additionally comprises extracting the resultant nucleic acid by cleaving the chemical linker through the addition of tris(2-carboxyethyl)phosphine (TCEP) or dithiothreitol (DTT) for a disulfide linker; palladium complexes or an allyl linker; or TCEP for an azide-masked hemiaminal ether linker.

In one embodiment, the resultant nucleic acid is extracted and amplified by polymerase chain reaction using the nucleic acid bound to the solid support as a template. The initiator sequence could therefore contain an appropriate forward primer sequence and an appropriate reverse primer could be synthesised.

In one embodiment, the terminal deoxynucleotidyl transferase (TdT) of the invention is added in the presence of an extension solution comprising one or more buffers (e.g., Tris or cacodylate), one or more salts (e.g., $Na^+$, $K^+$, $Mg^{2+}$, $Mn^{2+}$, $Cu^{2+}$, $Zn^{2+}$, $Co^{2+}$, etc. all with appropriate counterions, such as Cl) and inorganic pyrophosphatase (e.g., the *Saccharomyces cerevisiae* homolog). It will be understood that the choice of buffers and salts depends on the optimal enzyme activity and stability. The use of an inorganic pyrophosphatase helps to reduce the build-up of pyrophosphate due to nucleoside triphosphate hydrolysis by TdT. Therefore, the use of an inorganic pyrophosphatase has the advantage of reducing the rate of (1) backwards reaction and (2) TdT strand dismutation.

In one embodiment, step (b) is performed at a pH range between 5 and 10. Therefore, it will be understood that any buffer with a buffering range of pH 5-10 could be used, for example cacodylate, Tris, HEPES or Tricine, in particular cacodylate or Tris.

In one embodiment, step (b) is performed at a temperature greater than 37° C. Step (b) can be performed at greater than 50° C., or greater than 60° C.

In one embodiment, the reagents used in step (b) are removed by applying a wash solution. In one embodiment, the wash solution comprises the same buffers and salts as used in the extension solution described herein. This has the advantage of allowing the wash solution to be collected and recycled as extension solution in step (b) when the method steps are repeated.

Also disclosed is a kit comprising a terminal deoxynucleotidyl transferase (TdT) as defined herein in combination with an initiator sequence and one or nucleoside triphosphates, for example dATP.

The invention includes the nucleic acid sequence used to express the modified terminal transferase. Included within the invention are the codon-optimized cDNA sequences which express the modified terminal transferase. Included are the codon-optimized cDNA sequences for each of the protein variants.

The invention includes a cell line producing the modified terminal transferase.

The invention claimed is:

1. A modified terminal deoxynucleotidyl transferase (TdT) of a wild type TdT, or a truncated version of said modified TdT that retains TdT activity, wherein the wild type TdT has the amino acid sequence of SEQ ID NO: 1, and wherein said modified TdT or said truncated version thereof differs from said wild type TdT with amino acid modifications comprising:
   a. a modification at a residue corresponding to R193 of SEQ ID NO: 1, and/or
   b. a modification at two or more amino acid residues positions corresponding to E456, R457 and N473 of SEQ ID NO: 1;

wherein in de novo single-stranded DNA synthesis, said modified TdT or said truncated version thereof has, when compared to said wild-type TdT:
   1) Enhanced ability to incorporate 3'-O-reversibly terminated nucleotides;
   2) Enhanced ability to incorporate dATP;
   3) Enhanced ability to incorporate nucleotides at a temperature >37° C.; and/or
   4) Higher TdT catalytic activity.

2. The modified terminal deoxynucleotidyl transferase (TdT) or the truncated version thereof according to claim 1, wherein the amino acid modifications comprise said modification at the residue corresponding to R193 of SEQ ID NO: 1.

3. The modified terminal deoxynucleotidyl transferase (TdT) or the truncated version thereof according to claim 1, wherein the amino acid modifications comprise said modification at the residues corresponding to E456, R457, and N473 of SEQ ID NO: 1.

4. The modified terminal deoxynucleotidyl transferase (TdT) or the truncated version thereof according to claim 1, wherein the amino acid modifications comprise said modification at the residue corresponding to R193 of SEQ ID NO: 1, and said modification at the residues corresponding to E456 and N473 of SEQ ID NO: 1.

5. The modified terminal deoxynucleotidyl transferase (TdT) or the truncated version thereof according to claim 1, wherein the amino acid modifications comprise said modification at the residue corresponding to R193 of SEQ ID NO: 1, and said modification at the residues corresponding to E456, R457, and N473 of SEQ ID NO: 1.

6. The modified terminal deoxynucleotidyl transferase (TdT) or the truncated version thereof according to claim 1, wherein the amino acid modifications comprise said modification at the residue corresponding to E456G of SEQ ID NO: 1.

7. The modified terminal deoxynucleotidyl transferase (TdT) or the truncated version thereof according to claim 1, wherein the amino acid modifications comprise said modification at the residue corresponding to N473G of SEQ ID NO: 1.

8. The modified terminal deoxynucleotidyl transferase (TdT) or the truncated version thereof according to claim 1, wherein the amino acid modifications comprise said modification a the residue corresponding to R193H of SEQ ID NO: 1.

9. The modified terminal deoxynucleotidyl transferase (TdT) or the truncated version thereof according to claim 1, wherein the amino acid modifications comprise said modification at the residue corresponding to R457S of SEQ ID NO: 1.

10. The modified terminal deoxynucleotidyl transferase (TdT) or the truncated version thereof according to claim 1, wherein the amino acid modifications comprise said modification at the residue corresponding to E456G and N473G of SEQ ID NO: 1.

11. The modified terminal deoxynucleotidyl transferase (TdT) or the truncated version thereof according to claim 1, wherein the amino acid modifications comprise said modification at the residue corresponding to R193H, E456G R457S and N473G of SEQ ID NO: 1.

12. A method of nucleic acid synthesis, comprising: adding a nucleotide selected from dATP, dCTP, dGTP, or dTTP to an initiator oligonucleotide, in the presence of a terminal deoxynucleotidyl transferase (TdT) or a truncated version thereof of claim 1 prior to removing all reagents from the initiator oligonucleotide.

13. The method as defined in claim 12, wherein greater than 1 nucleotide is added.

14. A kit comprising a terminal deoxynucleotidyl transferase (TdT) or a truncated version thereof as defined in claim 1, in combination with an initiator oligonucleotide and 1 or more of dATP, dCTP, dGTP, and dTTP.

15. The method according to claim 12, wherein the nucleotide added comprises dATP.

16. The kit according to claim 14, comprising the TdT, the initiator oligonucleotide, and dATP.

* * * * *